US008439838B2

(12) United States Patent
Mogensen et al.

(10) Patent No.: US 8,439,838 B2
(45) Date of Patent: May 14, 2013

(54) INSERTER FOR TRANSCUTANEOUS SENSOR

(75) Inventors: Lasse W. Mogensen, Ballerup (DK); Magnus W. Göransson, Malmö (SE)

(73) Assignee: Unomedical A/S, Birkeroed (DK)

( * ) Notice: Subject to any disclaimer, the term of this patent is extended or adjusted under 35 U.S.C. 154(b) by 1027 days.

(21) Appl. No.: 12/303,494

(22) PCT Filed: Jun. 7, 2007

(86) PCT No.: PCT/DK2007/000273
§ 371 (c)(1),
(2), (4) Date: May 22, 2009

(87) PCT Pub. No.: WO2007/140783
PCT Pub. Date: Dec. 13, 2007

(65) Prior Publication Data
US 2010/0022863 A1    Jan. 28, 2010

Related U.S. Application Data

(60) Provisional application No. 60/811,563, filed on Jun. 7, 2006.

(30) Foreign Application Priority Data

Jun. 7, 2006    (DK) ................................. 2006 00770

(51) Int. Cl.
*A61B 5/00* (2006.01)
(52) U.S. Cl.
USPC ......................................................... 600/365
(58) Field of Classification Search ........................ None
See application file for complete search history.

(56) References Cited

U.S. PATENT DOCUMENTS

| | | |
|---|---|---|
| 1,592,462 A | 7/1926 | MacGregor |
| 2,047,010 A | 6/1936 | Dickinson |
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 11/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,610,240 A | 10/1971 | Harautuneian |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |

(Continued)

FOREIGN PATENT DOCUMENTS

| | | |
|---|---|---|
| DE | 4 342 329 A1 | 6/1994 |
| DE | 196 31 921 A1 | 3/1997 |

(Continued)

OTHER PUBLICATIONS

International Search Report completed Jan. 10, 2008 for International Application No. PCT/DK2007/000273.

(Continued)

*Primary Examiner* — Frederick Krass
*Assistant Examiner* — Dennis J Parad
(74) *Attorney, Agent, or Firm* — Brinks Hofer Gilson & Lione

(57) ABSTRACT

The invention relates to an inserter for a transcutaneous sensor comprising a sensor part e.g. for registration of the bloods content of glucose. The inserter comprises a needle unit comprising a needle hub and a carrier body, and a sensor housing. The sensor housing and the needle hub are releasably connected and when they are connected, the insertion needle is placed along the sensor e.g. surrounding the sensor wholly or partly. The carrier body guides the movement relative to the housing between a retracted and an advanced position. When released the needle unit and the sensor housing are forced by a spring unit to an advanced position where the needle and sensor are placed subcutaneously. The object of the invention is to provide a disposable inserter for a transcutaneous sensor which inserter is easy and safe for the user to handle during use and to dispose of after use.

18 Claims, 26 Drawing Sheets

U.S. PATENT DOCUMENTS

| | | | |
|---|---|---|---|
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,850,996 A | 7/1989 | Cree | |
| 4,863,016 A | 9/1989 | Fong et al. | |
| 4,878,897 A | 11/1989 | Katzin | |
| 4,890,608 A | 1/1990 | Steer | |
| 4,894,054 A | 1/1990 | Miskinyar | |
| 4,895,570 A | 1/1990 | Larkin | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olsen | |
| 5,020,665 A | 6/1991 | Bruno | |
| 5,024,662 A | 6/1991 | Menes et al. | |
| 5,067,496 A | 11/1991 | Eisele | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | Van den Haak | |
| 5,116,325 A | 5/1992 | Paterson | |
| 5,121,751 A | 6/1992 | Panalletta | |
| 5,129,884 A | 7/1992 | Dysarz | |
| 5,135,502 A | 8/1992 | Koenig, Jr. et al. | |
| 5,137,516 A | 8/1992 | Rand et al. | |
| 5,137,524 A | 8/1992 | Lynn et al. | |
| 5,141,496 A | 8/1992 | Dalto et al. | |
| 5,147,375 A | 9/1992 | Sullivan et al. | |
| 5,163,915 A | 11/1992 | Holleron | |
| 5,172,808 A | 12/1992 | Bruno | |
| 5,176,643 A | 1/1993 | Kramer et al. | |
| 5,176,650 A | 1/1993 | Haining | |
| 5,176,662 A | 1/1993 | Bartholomew et al. | |
| 5,186,712 A | 2/1993 | Kelso et al. | |
| 5,188,611 A | 2/1993 | Orgain | |
| RE34,223 E | 4/1993 | Bonaldo | |
| 5,205,820 A | 4/1993 | Kriesel | |
| 5,222,947 A | 6/1993 | D'Amico | |
| 5,232,454 A | 8/1993 | Hollister | |
| 5,248,301 A | 9/1993 | Koenig et al. | |
| 5,256,149 A | 10/1993 | Banik et al. | |
| 5,256,152 A | 10/1993 | Marks | |
| 5,257,980 A | 11/1993 | Van Antwerp et al. | |
| 5,267,963 A | 12/1993 | Bachynsky | |
| 5,269,799 A | 12/1993 | Daniel | |
| 5,271,744 A | 12/1993 | Kramer et al. | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,372,787 A | 12/1994 | Ritter | |
| 5,376,082 A | 12/1994 | Phelps | |
| 5,379,895 A | 1/1995 | Foslien | |
| 5,384,174 A | 1/1995 | Ward et al. | |
| 5,387,197 A | 2/1995 | Smith et al. | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,425,715 A | 6/1995 | Dalling et al. | |
| 5,429,607 A | 7/1995 | McPhee | |
| 5,429,613 A | 7/1995 | D'Amico | |
| 5,439,473 A | 8/1995 | Jorgensen | |
| D362,718 S | 9/1995 | Deily et al. | |
| 5,449,349 A | 9/1995 | Sallee et al. | |
| 5,451,210 A | 9/1995 | Kramer et al. | |
| 5,478,316 A | 12/1995 | Bitdinger et al. | |
| 5,490,841 A | 2/1996 | Landis | |
| 5,501,675 A | 3/1996 | Erskine | |
| 5,505,709 A | 4/1996 | Funderburk et al. | |
| 5,507,730 A | 4/1996 | Haber et al. | |
| 5,514,117 A | 5/1996 | Lynn | |
| 5,520,654 A | 5/1996 | Wahlberg | |
| 5,522,803 A | 6/1996 | Teissen-Simony | |
| 5,527,287 A | 6/1996 | Miskinyar et al. | |
| 5,533,974 A | 7/1996 | Gaba | |
| 5,540,709 A | 7/1996 | Ramel | |
| 5,545,143 A | 8/1996 | Fischell | |
| 5,545,152 A | 8/1996 | Funderburk et al. | |
| 5,549,577 A | 8/1996 | Siegel et al. | |
| 5,554,130 A | 9/1996 | McDonald et al. | |
| 5,558,650 A | 9/1996 | McPhee | |
| 5,562,629 A | 10/1996 | Haughton et al. | |
| 5,562,636 A | 10/1996 | Utterberg | |
| 5,573,510 A | 11/1996 | Isaacson | |
| 5,575,777 A | 11/1996 | Cover et al. | |
| 5,584,813 A | 12/1996 | Livingston et al. | |
| 5,586,553 A | 12/1996 | Halili | |
| 5,591,188 A | 1/1997 | Waisman | |
| 5,599,309 A | 2/1997 | Marshall et al. | |
| 5,599,315 A | 2/1997 | McPhee | |
| 5,599,318 A | 2/1997 | Sweeney et al. | |
| 5,628,765 A | 5/1997 | Morita | |
| 5,643,214 A | 7/1997 | Marshall | |
| 5,643,216 A | 7/1997 | White | |
| 5,643,220 A | 7/1997 | Cosme | |
| 5,662,617 A | 9/1997 | Odell et al. | |
| 5,665,071 A | 9/1997 | Wyrick | |
| 5,665,075 A | 9/1997 | Gyure et al. | |
| 5,676,156 A | 10/1997 | Yoon | |
| 5,681,323 A | 10/1997 | Arick | |
| 5,695,476 A | 12/1997 | Harris | |
| 5,697,907 A | 12/1997 | Gaba | |
| 5,700,250 A | 12/1997 | Erskine | |
| 5,702,371 A | 12/1997 | Bierman | |
| 5,704,920 A | 1/1998 | Gyure | |
| 5,709,662 A | 1/1998 | Olive et al. | |
| 5,714,225 A | 2/1998 | Hansen et al. | |
| 5,738,641 A | 4/1998 | Watson et al. | |
| 5,741,288 A | 4/1998 | Rife | |
| 5,752,923 A | 5/1998 | Terwilliger | |
| 5,807,316 A | 9/1998 | Teeple | |
| 5,807,348 A | 9/1998 | Zinger et al. | |
| 5,810,835 A | 9/1998 | Ryan et al. | |
| 5,817,058 A | 10/1998 | Shaw | |
| 5,820,598 A | 10/1998 | Gazza et al. | |
| 5,827,236 A | 10/1998 | Takahashi | |
| 5,833,666 A | 11/1998 | Davis et al. | |
| 5,843,001 A | 12/1998 | Goldenberg | |
| 5,848,990 A | 12/1998 | Cirelli et al. | |
| 5,851,197 A | 12/1998 | Marano et al. | |
| 5,858,001 A | 1/1999 | Tsals et al. | |
| 5,865,806 A | 2/1999 | Howell | |
| 5,899,886 A | 5/1999 | Cosme | |
| 5,911,705 A | 6/1999 | Howell | |
| 5,913,846 A | 6/1999 | Szabo | |
| 5,916,199 A | 6/1999 | Miles | |
| 5,919,167 A | 7/1999 | Mulhauser et al. | |
| 5,919,170 A | 7/1999 | Woessner | |
| 5,925,032 A | 7/1999 | Clements | |
| 5,935,109 A | 8/1999 | Donnan | |
| 5,947,931 A | 9/1999 | Bierman | |
| 5,947,935 A | 9/1999 | Rhinehart et al. | |
| 5,951,523 A | 9/1999 | Osterlind et al. | |
| 5,954,643 A | 9/1999 | VanAntwerp et al. | |
| 5,957,892 A | 9/1999 | Thorne | |
| 5,957,897 A | 9/1999 | Jeffrey | |
| 5,968,011 A | 10/1999 | Larsen et al. | |
| 5,975,120 A | 11/1999 | Novosel | |

| Patent No. | Date | Inventor |
|---|---|---|
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,379,335 B1 | 4/2002 | Rigon et al. |
| 6,387,076 B1 | 5/2002 | Van Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B2 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |

| | | |
|---|---|---|
| 2002/0072720 A1 | 6/2002 | Hague et al. |
| 2002/0074345 A1 | 6/2002 | Scheider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0066955 A1 | 3/2007 | Sparholt et al. |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |

| | | | |
|---|---|---|---|
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0213673 A1 | 9/2007 | Douglas | |
| 2007/0244448 A1 | 10/2007 | Lastovich et al. | |
| 2008/0269687 A1 | 10/2008 | Chong | |
| 2008/0312601 A1 | 12/2008 | Cane' | |
| 2009/0062767 A1 | 3/2009 | Van Antwerp et al. | |
| 2009/0326456 A1 | 12/2009 | Cross et al. | |
| 2010/0004597 A1 | 1/2010 | Gyrn et al. | |
| 2010/0137829 A1 | 6/2010 | Nielsen et al. | |
| 2010/0228226 A1 | 9/2010 | Nielsen | |
| 2010/0262078 A1 | 10/2010 | Blomquist | |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| JE | 10179734 | 8/1991 |
| JP | 7051251 A | 11/1995 |
| JP | 8187286 A | 7/1996 |
| JP | A-03-191965 | 7/1998 |
| JP | 2002-028246 A | 1/2002 |
| RU | 2 238 111 C2 | 12/2003 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A1 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/081012 A2 | 10/2002 |
| WO | WO 02/081013 A1 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |

| | | |
|---|---|---|
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/112521 A1 | 10/2010 |
| WO | WO 2011/012465 A1 | 2/2011 |
| WO | WO 2011/015659 A1 | 2/2011 |

OTHER PUBLICATIONS

"Why inset®?" inset® infusion set product overview; http://web.archive.org/web/20040906102448/http://www.infusion-set.com/Default.asp?ID=108; two pages.

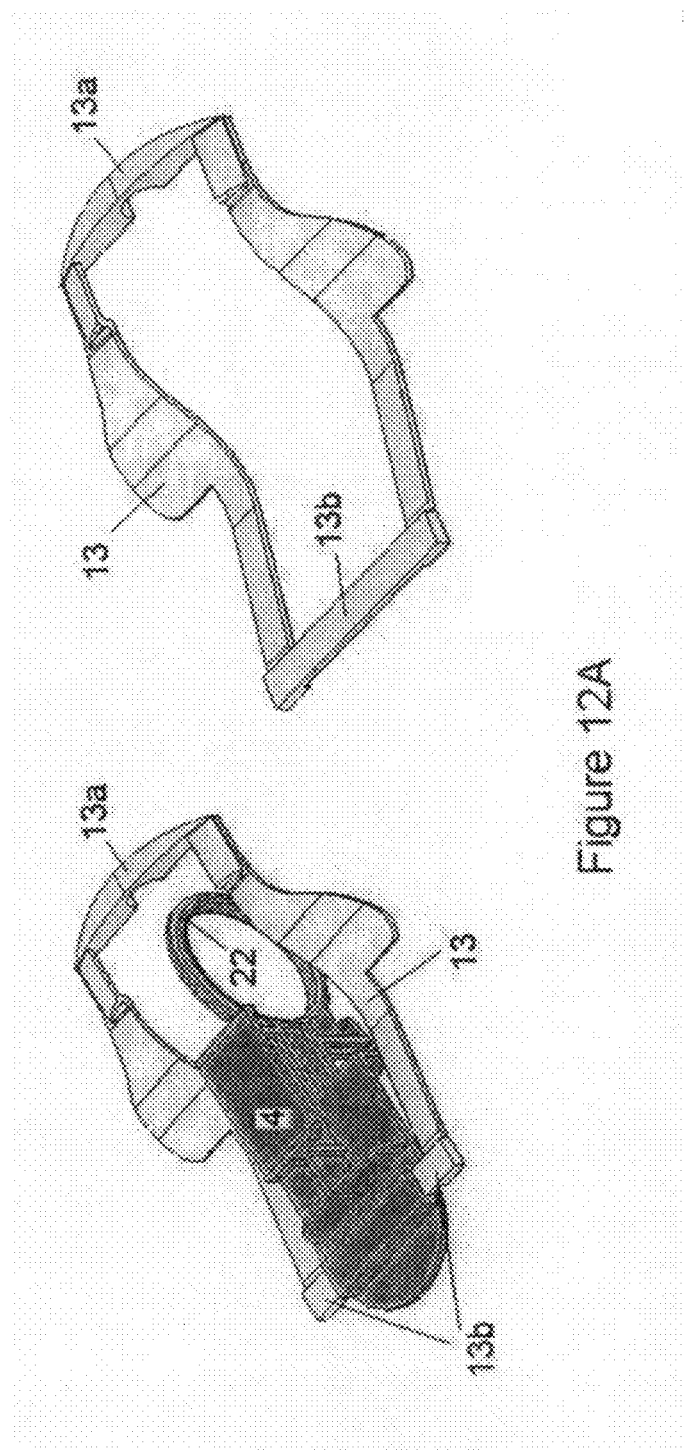

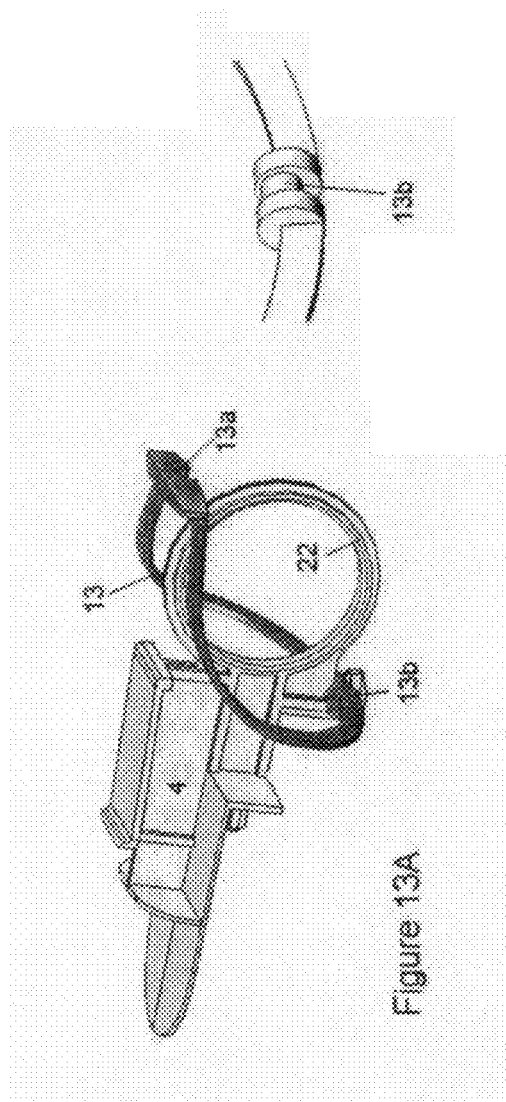

A
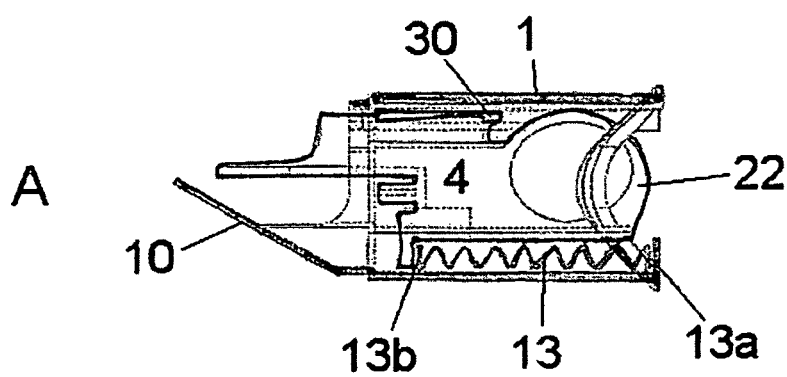
B
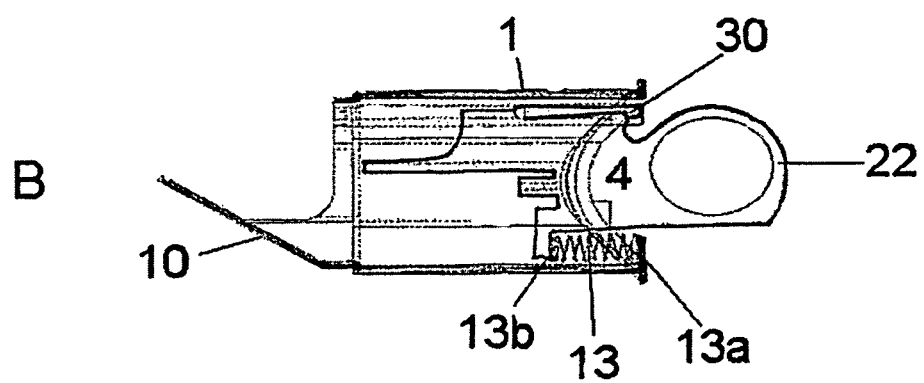
Fig. 15

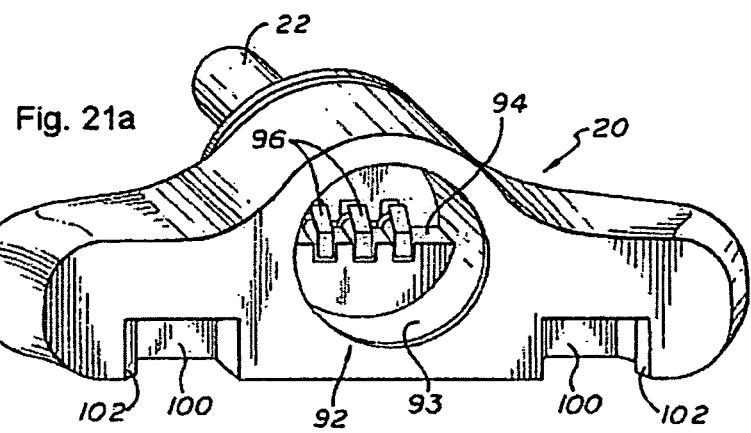
Fig. 21a
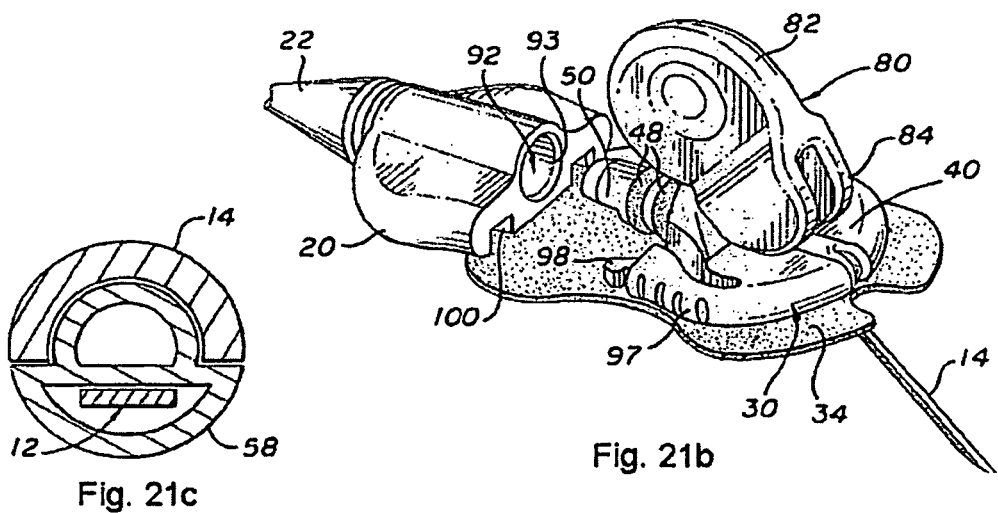
Fig. 21c
Fig. 21b

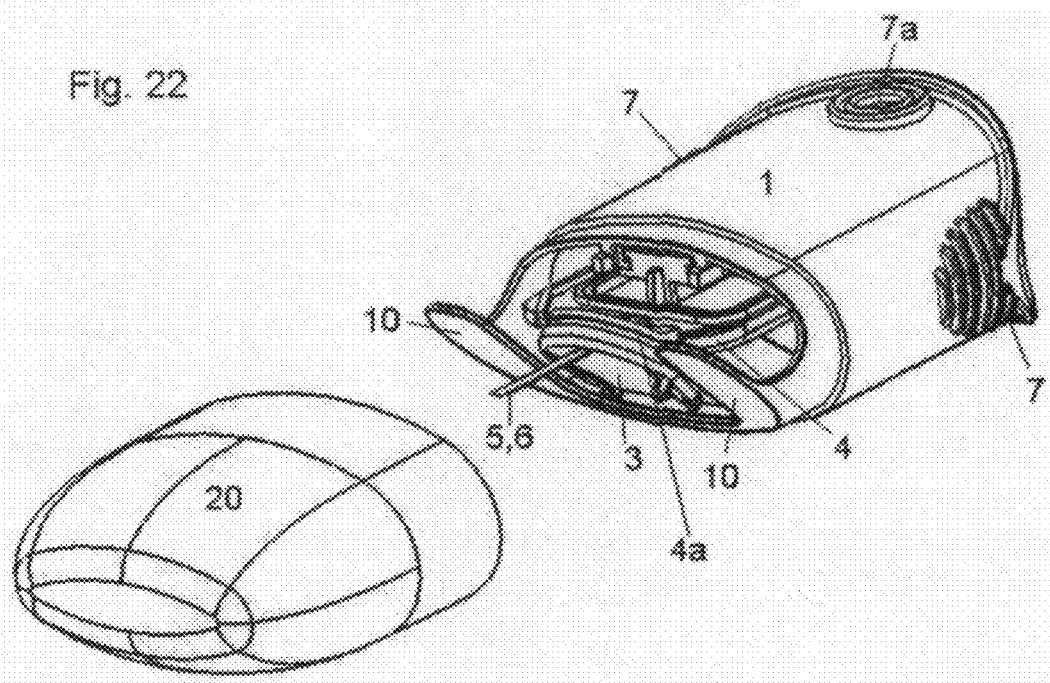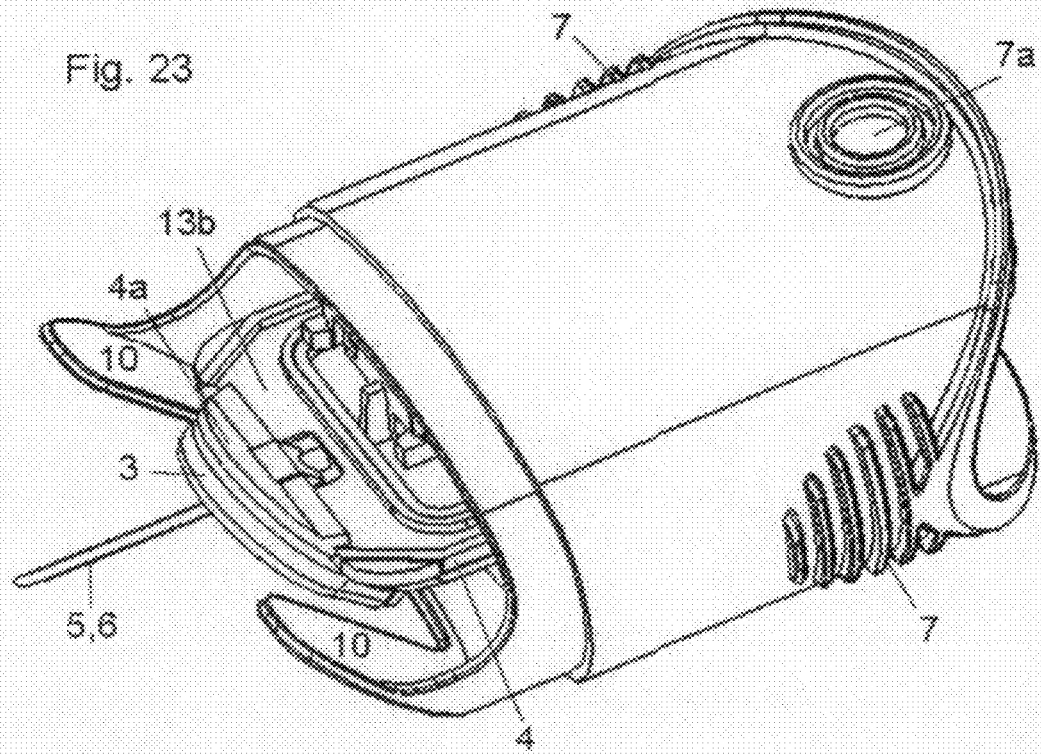

INSERTER FOR TRANSCUTANEOUS SENSOR

This application claims the benefit under 35 U.S.C. §371 of International Application No. PCT/DK2007/000273, filed Jun. 7, 2007, which claims the benefit of Danish Patent Application No. PA 2006 00770, filed Jun. 7, 2006, and U.S. Provisional Application Serial No. 60/811,563, filed Jun. 7, 2006. These references are incorporated herein in their entirety.

TECHNICAL FIELD

The invention relates to an inserter for a transcutaneous sensor which is able to register components in the blood of a patient such as a glucose sensor. The inserter comprises a needle unit with an insertion needle which before and during insertion s connected to a sensor housing comprising a sensor part which is to be placed subcutaneously in a patient.

BACKGROUND OF THE INVENTION

US 2002/0077599 A1 concerns an inserter for a low-profile, angled infusion set which inserter comprises an inserter housing having a bottom wall, a retainer slidably connected to the inserter housing for movement between retracted and extended positions in a direction substantially parallel with the bottom wall. The inserter also comprises a base member connected to the outer surface of the inserter housing. The retainer is adapted to releasably receive a sensor housing. When used the retainer 30 moves forward and causes the needle 27 and the sensor 26 to pierce the skin at a proper angle and enter into the subcutaneous layer at a proper distance. The sensor housing 28 can then be released from the inserter assembly 10 by depressing the release button 66. Afterwards the mounting pad 80 is secured to the skin and the needle 27 is removed, thus leaving the sensor 26 in place. This reference concerns a rather complex structure and the complexity necessitates the use of two housing portions, an upper and a lower which portions may be constructed of any suitable material, and can be retained together through screws (23, FIG. 5), interlocking tabs, adhesive, heat-staking or a combination thereof, or any other well-known fastening means.

An inserter described in U.S. Pat. No. 6,293,925 B1 comprises an injector and an insertion set. The injector is designed to place a needle through the skin at a selected insertion angle and with a controlled force and speed of insertion. The injector comprises a spring-loaded plunger having a head for receiving and supporting the insertion set in a position with an insertion projecting outwardly for transcutaneous placement through the skin of a patient. The plunger is designed for retraction and retention to a locked position with a drive spring compressed in a manner applying a predetermined spring force to the plunger head. FIGS. 30 and 31 illustrate how the subcutaneous insertion set 14 is assembled with the injector when preparing the injector for use.

DESCRIPTION OF INVENTION

The object of the invention is to provide a simple, non-expensive inserter for a transcutaneous sensor which inserter would be easy and safe for the user to handle during use and to dispose of after use.

The invention concerns a disposable, low-profile inserter for a transcutaneous sensor which inserter comprises a housing, a sensor housing, a needle hub, a spring unit and a carrier body, where the housing is provided with guiding means on the internal surface for securing the movement of the carrier body,
the sensor housing comprises a sensor to be placed subcutaneously,
the needle hub comprises a needle for piercing of the skin,
the sensor housing and the needle hub are releasably fastened to each other and when fastened to each other the needle is adjoined the sensor; in one embodiment the needle is placed at least partly surrounding the sensor;
the carrier body is provided with guiding means on the external surface securing the movement of the carrier body relative to the housing when moving between a retracted and an advanced position,
the carrier body is connected to release means, and when the release means are manipulated, the carrier body, the sensor housing and the needle hub are forced by the spring unit to an advanced position where the needle and a part of the sensor will be placed subcutaneous when the user holds the device against the skin,
the needle hub and the carrier body are provided with unreleasable interacting locking means.

"Adjoined" means that the needle is placed adequately close to the sensor to assure the subcutaneously insertion of the sensor whether the sensor is placed inside, beside or on the outer side the insertion needle.

According to one embodiment of the invention the needle hub and the carrier body are created as a single unit e.g. by welding together a movable part of the housing and a needle hub or e.g. by fastening an insertion needle directly to a movable part of the housing. The unreleasable connection could be formed e.g. by gluing, welding or by mechanically locking the two units to each other.

In one embodiment the unreleasable connection between the carrier body and the needle hub is formed by making openings in a part of the needle hub which is covered by a continuous or coherent surface part of the housing, and by making corresponding projections in the carrier body. When the housing is placed around the needle unit ("around" meaning that material of the housing covers the needle unit on at least two opposite sides) either the elasticity of the housing will squeeze the two opposite sides together and thereby squeeze the needle hub and the carrier body together, or the confined space created by two opposite sides of an essentially rigid housing will force the projections of the carrier body and the openings of the needle hub together and form an unreleasable connection between the carrier body and the needle hub as the openings of the needle hub and the projections of the carrier body fit perfectly together.

According to another embodiment of the invention the needle unit is locked to the inserter after use. When the needle unit is locked to the inserter after use it will be possible for the user to remove both the inserter and the needle unit by only grabbing the inserter, instead of the user holding on to both inserter and needle unit after use. According to the embodiment shown in FIGS. 1-3 the needle unit is locked to the inserter because the needle unit can only move in a confined space. The confined space is formed by the Walls of the U-shaped housing on three sides, and by the guiding means of the housing and the needle unit on two sides as the guiding means prevents sideways movements and by the stopper 12 as the stopper 12 prevents the needle unit from moving forward beyond a fixed point.

According to another embodiment of the invention it is possible to move the needle unit back from the advanced position where the needle can pierce the skin of a patient to a retracted position in order to diminish the risks of getting into contact with the used needle.

According to another embodiment of the invention the lower part of the housing—where the lower part of the housing is the side closest to the user during insertion—could be prolonged and turned upward in relation to the base line (the base line is a line parallel to the needle but at a lower level where a "lower level" means a level closer to the user, normally the level provided by the lower side of the housing). This prolongation or projection of the lower part provides an appropriate contact between the skin of the patient and the inserter in order to have the sensor inserted in a proper angle, and also the prolonged or projecting part lifts up the mounting pad to a proper position for contact with the skin.

In one embodiment the ends of the projecting part are positioned above the line formed by the needle/sensor in front of the end of the insertion needle when the needle unit is in a retracted position. This makes it necessary to provide an opening in the prolongation in order for the needle/sensor to be able to pass through. According to the embodiment of FIGS. 1-3 this is obtained by separating the projecting part into two legs. In this embodiment the projecting part is formed as a mathematical continuous curvature but it could also be non-continuous, i.e. being provided with one or more breaks.

In another aspect of the invention the housing is made out of a single piece of material. That the needle hub housing is constructed of one piece of material means that no screws or the like is needed to assemble or fasten the casing surrounding the carrier body and the inserter set. The housing could be produced by molding, i.e. injection molding or by any other known technology. Also the housing could be produced as e.g. two halves which afterwards are glued or welded together. The housing could be made of plastic or metal or any other suitable material having the necessary mechanical properties.

The inserter according to the invention is of a simple construction and consists of relatively few parts and thus it will be less expensive to produce and assemble. This renders the inserter suitable for use as a disposable product.

In yet another embodiment the housing is formed of a single U-shaped piece of material. The housing is U-shaped which means that it is constructed of a rectangular or elliptic piece of flat material which is bent in such a way that the ends of the material—seen from the side—forms two substantial parallel legs connected in one end with a straight or arched line, where the legs are not necessarily of the same length. The material is of a bend form which does not necessarily mean that it is constructed by bending; it could e.g. be molded in a bend form. When the housing is U-shaped the part called the lower leg is the leg in contact with the user when the inserter is positioned for insertion of the infusion device.

In another embodiment the housing is formed as a piece of pipe with a rounded or poly-sided cut-through profile.

In yet another embodiment the spring unit is fastened to the housing in a first position and to the carrier body or the needle unit in a second position, where the first position is situated closer to the front end of the housing than the second position when the spring unit is biased. The front end of the housing is the end of the housing nearest the user during insertion. This feature will result in that the carrier body and the needle hub together are pulled forward relative to the housing when the release means are activated. The spring unit could be made of any material which retracts to a relaxed unbiased position, e.g. it is made of rubber, plastic or metal.

The invention also concerns an inserter for a transcutaneous sensor comprising a set housing (1), a sensor housing (3), a needle hub (2), a spring unit (13) and a carrier body (4), where the housing (1) is provided with guiding means (9a, 9b, 9c) on the internal surface for guiding the movement of the carrier body (4), the sensor housing (3) comprises a sensor part (5) to be placed subcutaneously, the needle hub (2) comprises an insertion needle (6) for piercing of the skin, the sensor housing (3) and the needle hub (2) are releasably connected to each other, and when they are connected, the insertion needle (6) is adjoined to the sensor part (5), the carrier body (4) is provided with guiding means (9e, 9d, 9f) on the external surface which guides the movement relative to the housing (1) between a retracted and an advanced position, the spring unit (13) is connected to release means (7) and when the release means (7) are activated, the sensor housing (3), the needle hub (2) and the carrier body (4) are forced by the spring unit to an advanced position where the needle (6) and sensor part (5) can be placed subcutaneously; the needle hub (2) and the carrier body (4) are provided with unreleasable interacting locking means the lower base of the housing (1) is formed with a projecting part (10), and the projecting part (10) forms an angle with the longitudinal direction of the insertion needle (6) indicating the correct insertion angle for the user during insertion.

According to an embodiment of this inserter a part of the projecting part (10) is positioned above the line along which the insertion needle (6) can move and a part of the projecting part (10) is positioned beyond said line.

DESCRIPTION OF THE DRAWINGS

The invention is explained in greater detail below with reference to the accompanying drawings wherein a preferred embodiment of the invention is shown.

FIG. 12A shows a spring unit similar to the fourth embodiment seen from above/front;

FIG. 13A shows a secondary embodiment with a circular spring seen from the side;

FIG. 15 shows a seventh embodiment with a coiled spring unit seen from the side in (A) a forward position and (B) a retracted position;

FIG. 21 shows a known transcutaneous sensor intended for manual insertion,

FIG. 22 shows an inserter for a transcutaneous sensor together with a hard top moved away from the protective position, FIG. 23 shows an inserter for a transcutaneous sensor after release of the spring.

Figure 1:
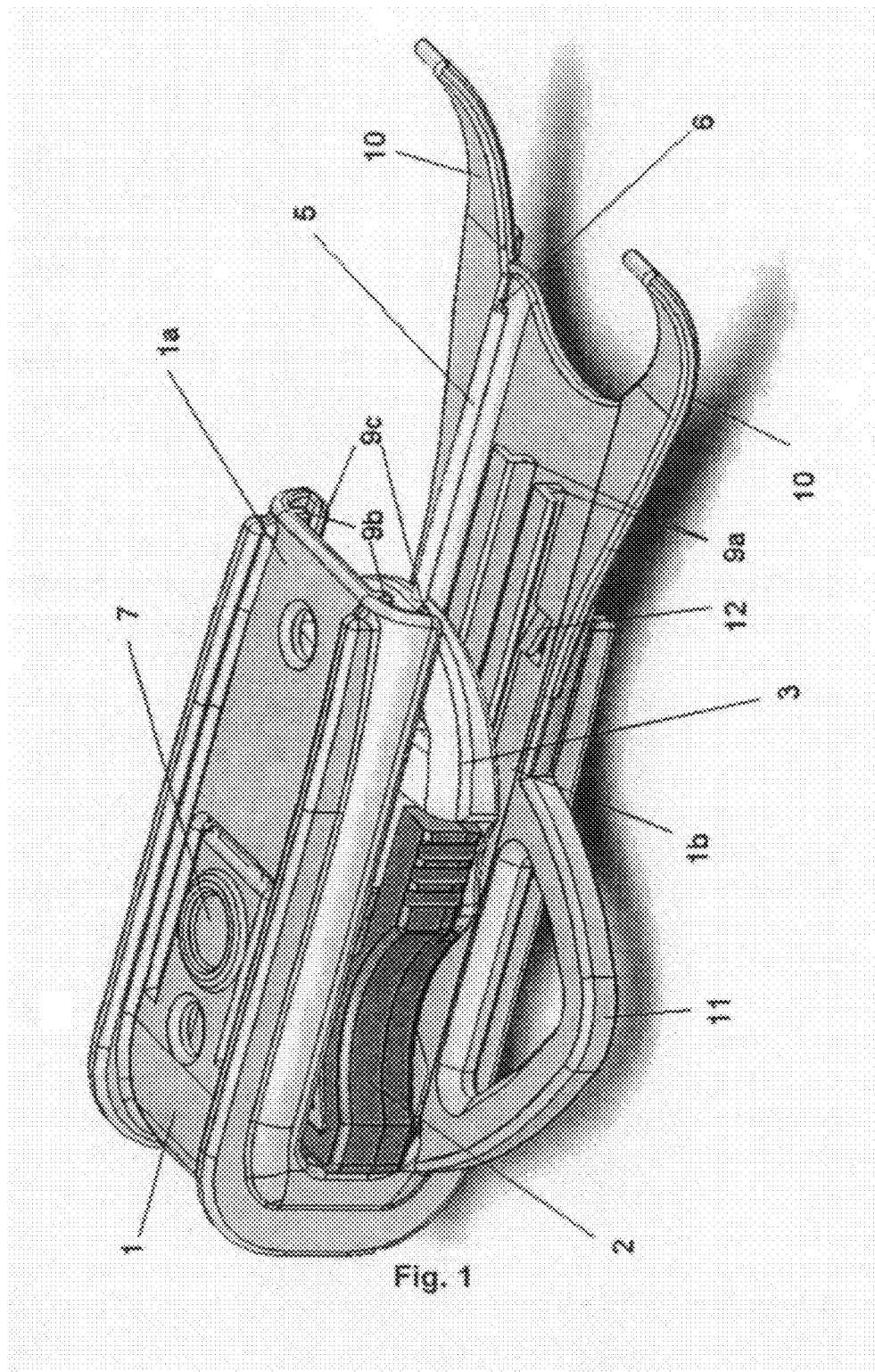
FIG. 1 is an upper/side view of an embodiment of the inserter of the invention with the transcutaneous sensor in a retracted position.
Figure 2:
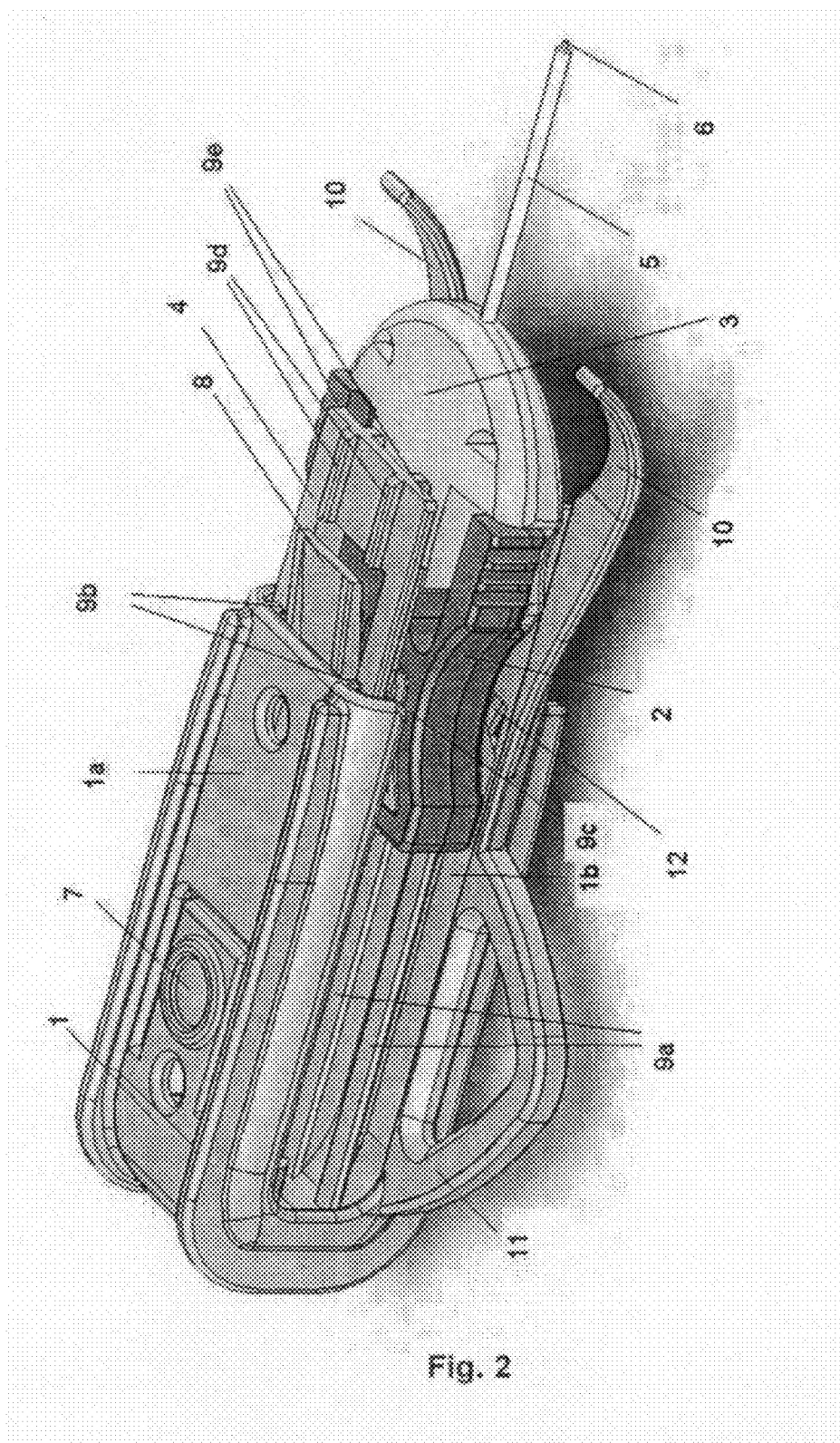
FIG. 2 is an upper/side view of the inserter with the transcutaneous sensor in an advanced position.
Figure 3:
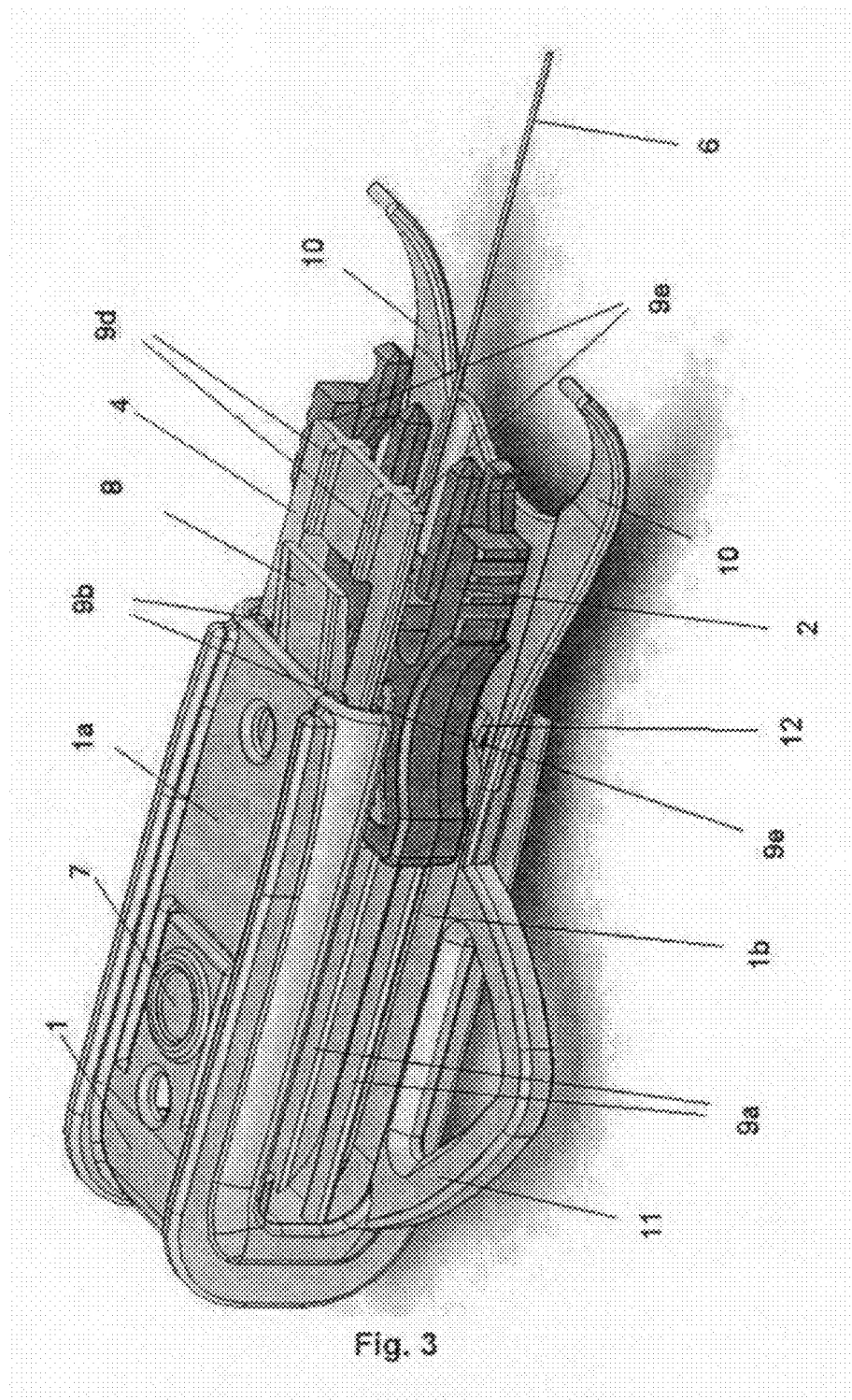
FIG. 3 is an upper/side view of the inserter with the transcutaneous sensor in an advanced position where the sensor housing has been detached from the needle unit.

The inserter set of FIGS. 1-3 comprises a housing 1, a needle unit which in this embodiment is constructed of a needle hub 2 comprising an insertion needle 6 and a carrier body 4 unreleasably connected to the needle hub 2, and a sensor housing 3 comprising a laterally projecting sensor part 5.

Figure 4:
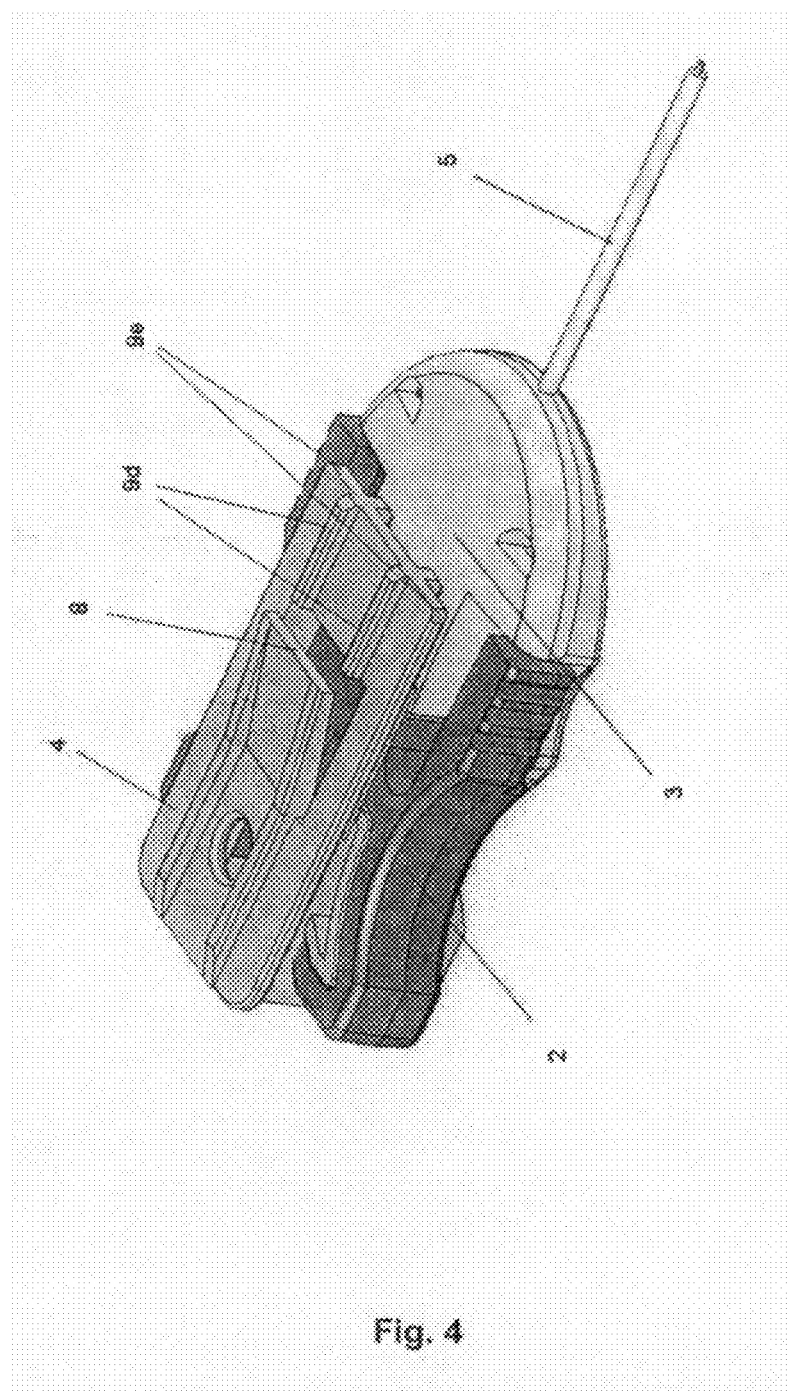
FIG. 4 is an upper/side view of the needle unit attached to the sensor housing.

The housing 1 is provided with a release button 7 which button when activated will release the spring unit 13 and cause the needle unit 2, 4 and the sensor housing 3 to move forward to an advanced position. When the release button 7 is activated, a flexible part 8 of the needle unit is pushed down and released from a not shown stop. The flexible part 8 is shown on FIGS. 2, 3 and 7 where the needle unit is in an advanced position and on FIG. 4 where the needle unit is shown isolated from the housing 1.

FIGS. 1-3 and 5-7 show an embodiment of the invention wherein the housing 1 is U-shaped having an upper leg 1a and a lower leg 1b. In this embodiment the upper and the lower leg are parallel and connected in one end through a piece of material approximately of the same length as the height of the needle unit 2, 4. The distance between the upper and the lower leg 1a, 1b will depend on height and general shape of the needle unit 2, 4 connected with the sensor housing 3 and also the distance between the upper and lower leg 1a, 1b should be sufficient to comprise the guiding means 9a, 9b, 9c which keep the needle unit 2, 4 and sensor housing 3 in place during traveling between the retracted and advanced position.

The guiding means of the housing in FIGS. 1-3 comprises two opposite and outward L-profiles 9a standing up from the lower leg 1b, flanges 9b extending downwardly from the upper leg 1a and flanges 9b extending inwardly from side parts of the upper leg 1a being in contact with the sides 9e of the needle unit 2, 4. The corresponding guiding means on the needle unit 2, 4 comprise at the bottom side of the needle unit 2, 4 two inward L-profiles (not shown in figures) which profiles correspond to the outward L-profiles on the housing 1, see FIG. 5, and on the upper side of the needle unit 2, 4 two flanges 9d are standing up from the top side keeping contact with the upper leg 1a and the flanges 9b.

At the end of the lower leg 1b two upwardly bend parts 10 are formed. These parts 10 indicate the correct insertion angle for the user when the user inserts the cannula. Also the parts 10 will assure that a mounting pad 14 placed in connection with the sensor housing 3 will be in correct and ready position when the sensor part 5 is inserted.

The essentially triangular profile 11 extending from the lower leg 1b is provided for facilitating handling as the total functional inserter set is quite small and else can be difficult to handle if the user has reduced dexterity.

Figure 6:
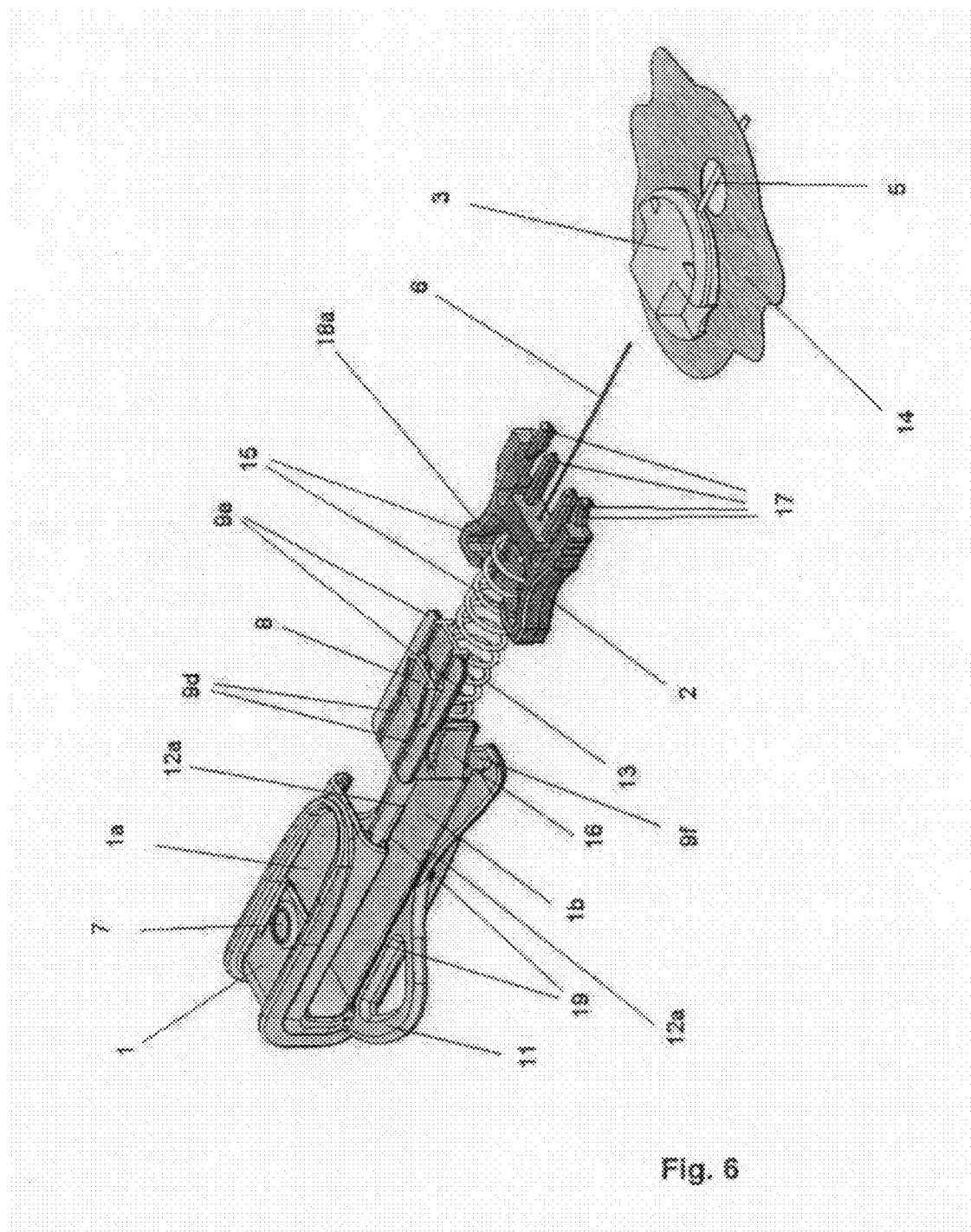
FIG. 6 is an upper/side exploded view of the inserter shown in FIG. 5 with the transcutaneous sensor.
Figure 7:
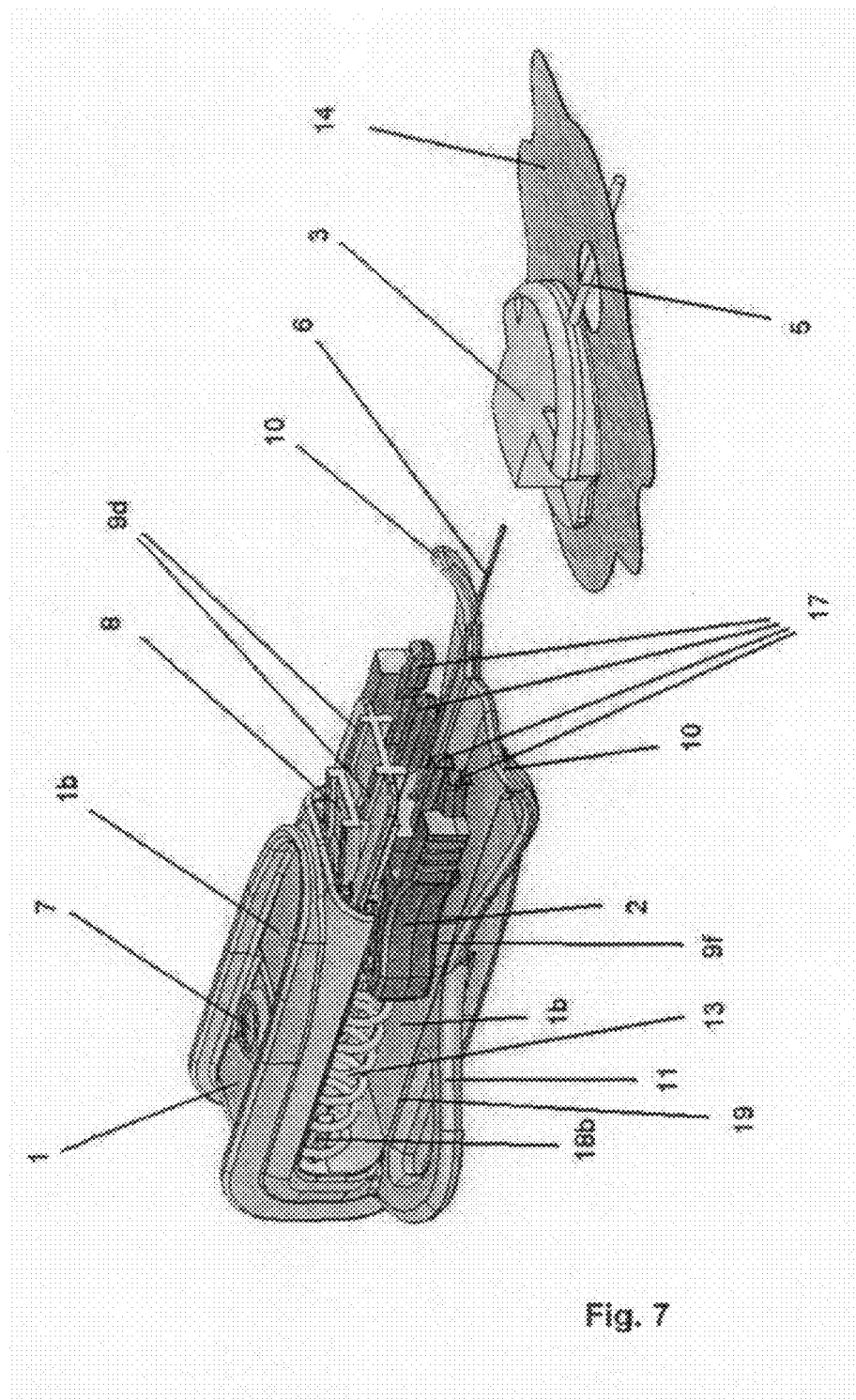
FIG. 7 is an upper/side view of the inserter shown in FIG. 5 where the needle unit is detached from the sensor housing and in an advanced position.

The spring unit 13 that pushes the needle unit 2, 4 forward when the release button 7 is activated, is shown in FIGS. 6 and 7. The spring unit 13 is placed between the housing 1 and the needle unit 2, 4 at the closed end of the U-shaped housing 1. The spring unit 13 is fastened to a protrusion 18a at the back end of the needle hub 2 and to a protrusion 18b on the inside of the housing 1. The spring unit 13 may be any suitable spring but in this embodiment the spring unit 13 is preferably a coil spring which pushes the needle unit 2, 4 away from the house ending.

The spring unit 13 could also be a flat spring placed between the housing 1 and the needle unit 2, 4 at the closed end of the U-shaped housing 1, or the spring unit 13 could form an elastic connection between the front of the housing 1 and the back of the needle unit 2, 4 pulling the needle unit 2, 4 forward.

In order to control the forward movement of the needle unit 2, 4 when the release button 7 is used, the lower leg 1b of the housing 1 is provided with a stopper 12. In the embodiment in FIGS. 1-3 the needle unit 2, 4 stops moving forward when a corresponding protrusion on the needle unit 2, 4 hits the stopper 12. In the embodiment in FIGS. 5-7 two flanges 9f move in tracks 19 formed as grooves in the lower leg 1b and the stopper 12a is provided as the flanges 9f touches the end of one or both of the tracks 19.

If there is no stopper 12 to stop the needle unit 2, 4 from moving forward, the needle unit 2, 4 will stop when the front of the needle unit touches the skin of the user. The use of a stopper 12 will make it easier to control the dept of insertion, and also the stopper 12 can lock the needle unit 2, 4 to the housing 1 making it possible to remove inserter and needle unit 2, 4 as a single item after use.

In another preferred embodiment the stopper 12 is created by the ends of the upper and lower legs 1a and 1b of a U-shaped housing 1. When both or one of the ends of the legs 1a and 1b are turned inwardly, the leg ends restrict the distance between the upper and the lower leg 1a, 1b at the open end of the U-shaped housing. When this distance is restricted to less than the height of the needle unit 2, 4, the inwardly turned leg ends perform as a stopper 12.

Figure 5:
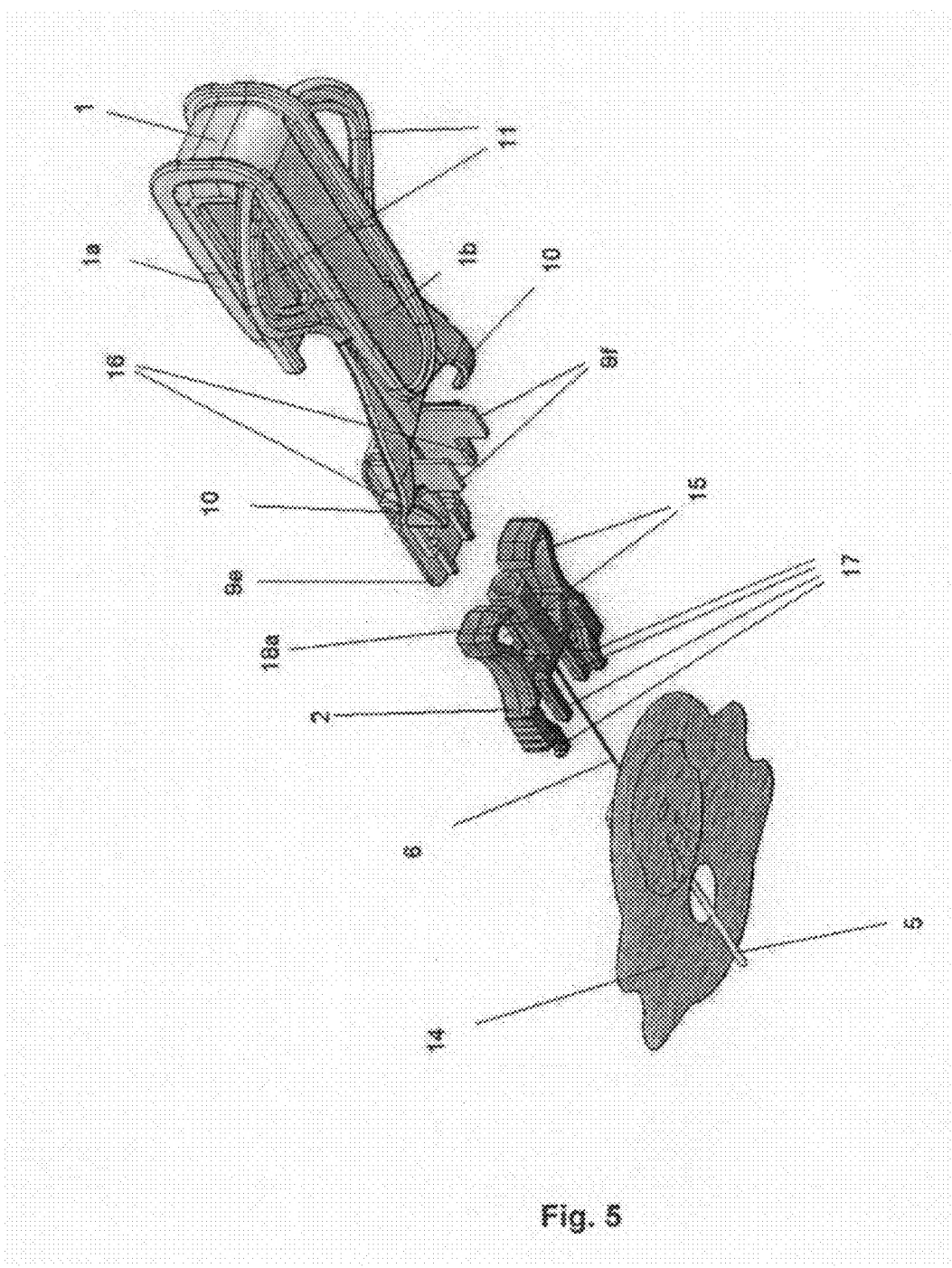
FIG. 5 is a lower/side exploded view of another embodiment of the inserter with the transcutaneous sensor.

In FIG. 5 the needle hub 2 is shown detached from the sensor housing 3 and the carrier body 4. In this preferred embodiment the needle hub 2 comprises two openings 15 in the rear half which openings 15 correspond to two projections 16 on the carrier body 4. When the projections 16 are placed in the openings 15, the needle hub 2 and the carrier body 4 are locked relatively to each other in the horizontal plane (in this embodiment the horizontal plane is the plane perpendicular to the contact surfaces between the openings of the needle hub 2 and the projections of the carrier body 4). When the needle unit 2, 4 comprising the joined needle hub 2 and carrier body 4 is placed in the housing 1, the legs 1a and 1b of the housing 1 cover the needle unit 2, 4 on two opposite sides and prevent movements in the vertical direction.

When the inserter set is produced and prepared for use, it will normally be delivered to the user in packed, set and sterilized condition being ready for use. When the user opens the package, the needle unit 2, 4 is connected to the sensor housing 3, and the transcutaneous sensor is in a retracted position. A mounting pad 14 is placed on the lower side of the sensor housing 3 and the sticky side of the mounting pad is covered with release paper. The user removes the release paper from the mounting pad and places the base part 1b, 10 of the inserter against the skin in an adequate angle; where after the user pushes the release button 7.

When pushing the release button 7 the needle unit 2, 4 together with the sensor housing 3 are released and pushed forward to the advanced position, and the sensor will be placed subcutaneously as the insertion needle 6 placed along the sensor part 5 pierces the skin.

The sensor could be of a known type as for example described in U.S. Pat. No. 5,586,553 where an insertion set (10) includes a rigid hollow slotted insertion needle (14) for quick and easy transcutaneous placement of a cannula (15) comprising a distal segment (16) having one or more sensor electrodes (18) exposed to patient fluid through a window (19) in the cannula (15). When the insertion needle (14) is withdrawn the cannula (15) is left with the sensor distal segment (16) and the sensor electrodes (18) in place at the selected insertion site.

The sensor housing according to this document comprises two guide openings and two locking openings in addition to the through bore. These openings are symmetrically shaped about a plane including the central axis of the through passageway and extending perpendicular to the rear side. The guide openings are elongated openings of a substantially square cross section which openings are adapted to receive mating guide pins 17 on a connecting needle or connecting hub. In FIGS. 3, 5, 6 and 7 where the needle unit 2, 4 is separated from the sensor housing 3 it is possible to see the guide pins 17 of the needle hub 2.

When the sensor part 5 and the sensor housing 3 covered with the mounting pad 14 is in place, the user unlocks the sensor housing 3 from the needle unit 2, 4 and removes the remains of the inserter set which comprises the housing 1 and the needle unit which is locked to the housing 1. In EP patent no. 688232 an appropriate releasable connection between a sensor housing and a needle hub is illustrated and the example is hereby incorporated by reference.

In order to dispose of the used inserter remains in a secure way, the user can pull the needle unit 2, 4 back into a retracted position and replace the inserter remains in the opened package.

After having disposed of the inserter and the needle unit the user can connect the sensor housing 3 which is now fastened to the user's skin, to a connecting hub.

The connecting hub can be connected to a luer coupling member through a hose. Through the luer coupling it is possible to administer a suitable therapeutical substance, such as insulin from a pump. The connecting hub can also be a closing part with a suitable entrance for the inserting needle of a syringe. Such a closing part can stay in position for up till three days while the user can have medication, e.g. insulin injected through the entrance in order to reduce trauma to the skin.

Figure 8:
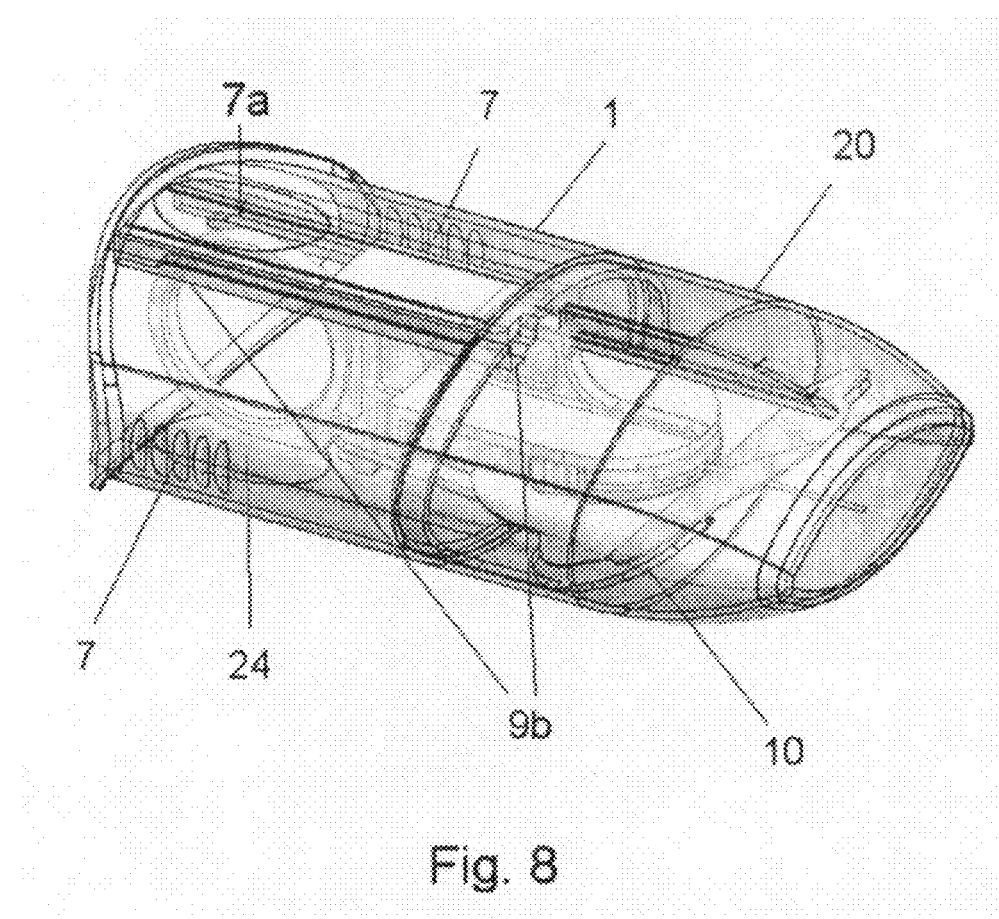
FIG. 8 is an upper/side view of a third embodiment of an inserter placed ready for delivery.
Figure 9:
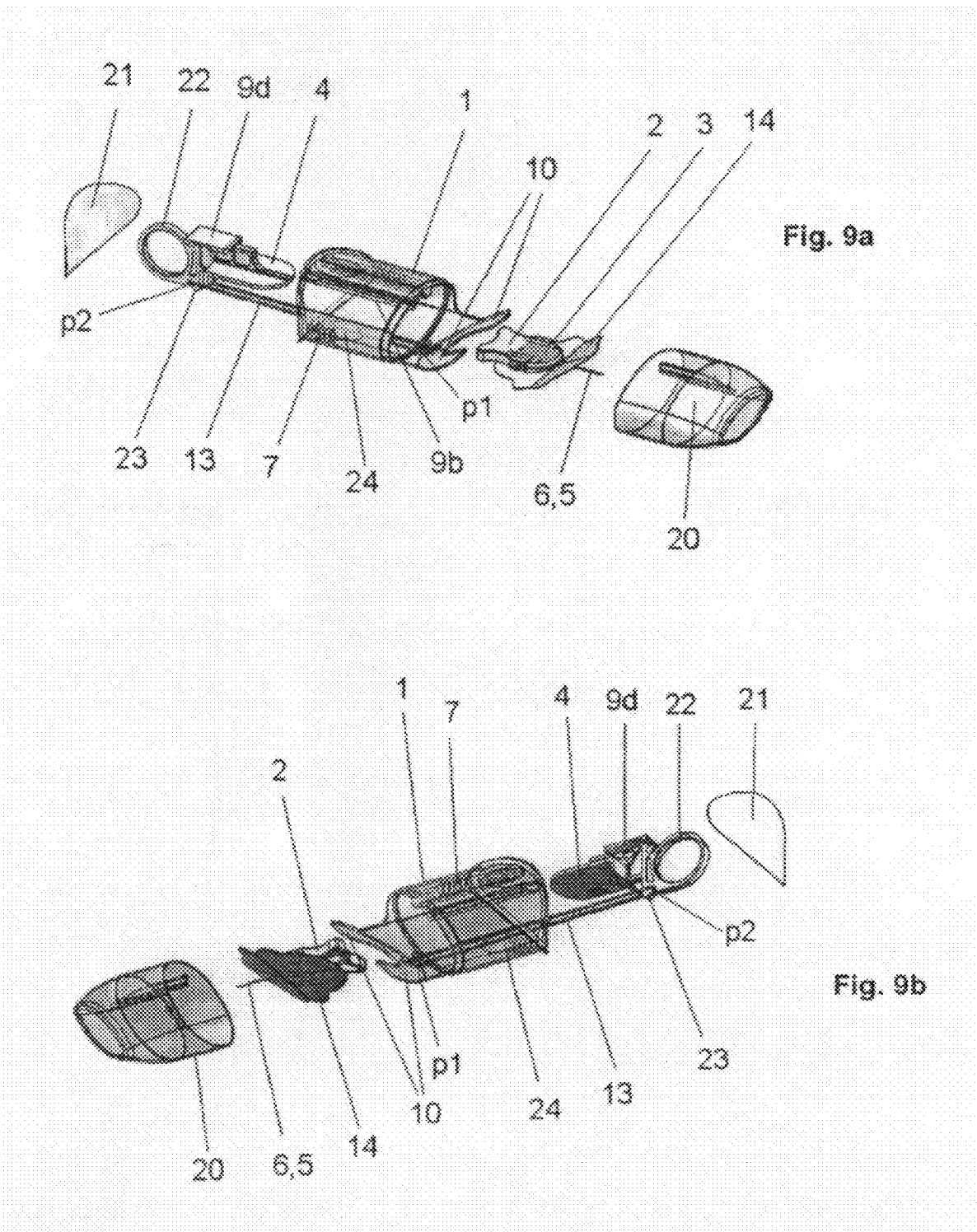
FIGS. 9a and b show an exploded view of the third embodiment.
Figure 10:
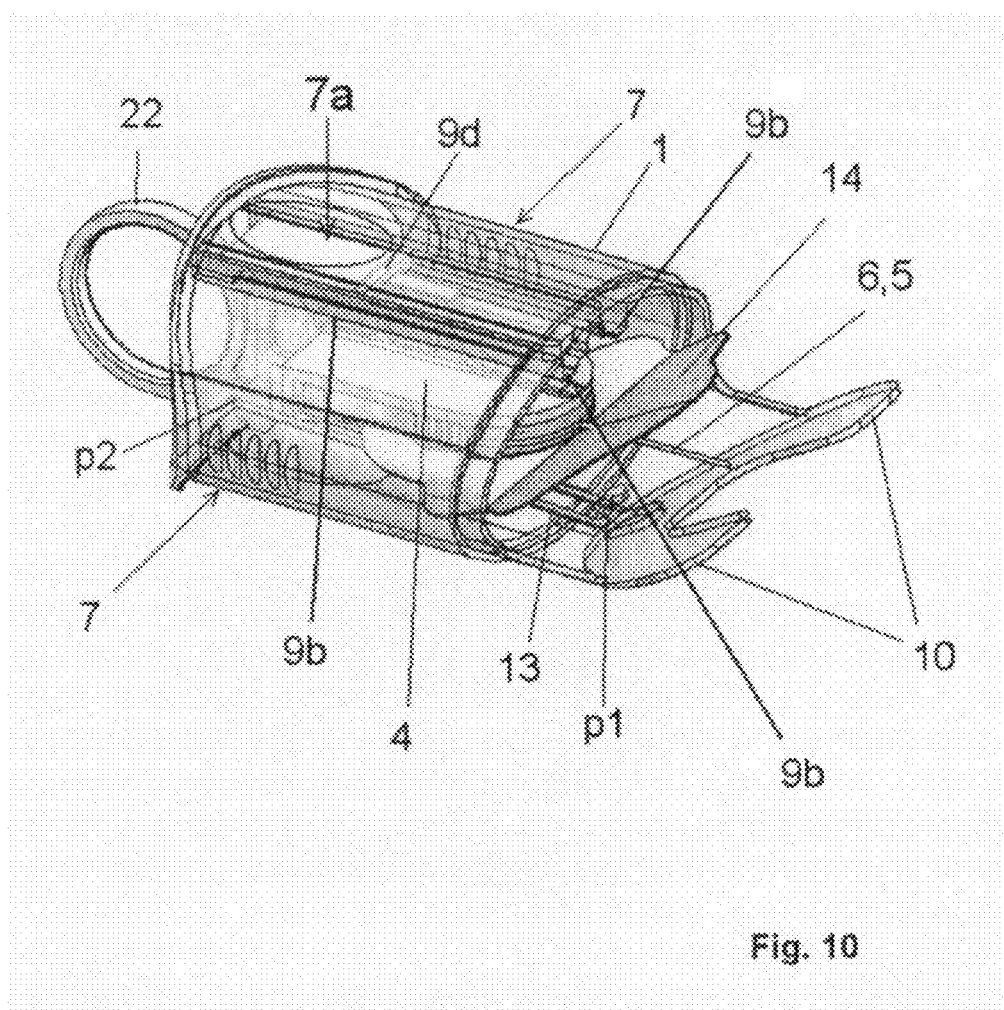
FIG. 10 shows the carrier body of the third embodiment in a retracted position ready for insertion.

The inserter set according to a third embodiment shown in FIGS. 8-10 comprises a housing 1, a needle unit constructed of a needle hub 2 comprising an insertion needle 6 and a carrier body 4 unreleasably connected to the needle hub 2, and a sensor housing 3 comprising a sensor part 5.

In FIG. 8 it is shown how this embodiment could be delivered: the needle unit 2, 4 is in a relaxed, i.e. non-biased or just slightly biased forward position and the needle is covered with a hard case top 20 which has to be removed from the device before use. The housing 1 is formed as a piece of pipe with an oval cut-through profile. Opposite the hard case top 20 the housing 1 is covered with a removable flat cover 21. The flat cover can be provided with an adhesive for assuring the tight closure between the cover 21 and the housing 1 or it can be welded to the housing, and any kind of cover which at the same time has the necessary strength to resist transportation and can provide heretical sealing of the device will do. The needle unit 2, 4 is unreleasably connected to a handle 22 which handle on the lower side is provided with a projection 23 for fastening of a spring unit 13 (see FIGS. 9a and 9b). The upper side of the carrier body 4 is provided with guiding means 9d having the form of a rectangular plate, the guiding means 9d of the carrier body 4 fit into guiding means 9b of the housing 1 having the form of downward L-profiles.

The combination of the L-profiles and the rectangular plate assures that the carrier body has limited possibilities for moving up and down, and is lead along the wall of the housing 1 in a very controlled manner. The spring unit 13 in this embodiment consists of elastic in the form of an O-ring. The spring is fastened to the lower front part of the housing 1 at the position p1 and the lower part of the carrier body 4 at position p2. In this embodiment the spring unit 13 is fastened behind—and beyond—the carrier part of the carrier body 4 which causes the carrier body 4 to get into a slightly tilted position when the spring is biased as only the lower part of the carrier body 4 is pulled forward by the spring unit 13, and this tilted position can lock or support the locking of the carrier body 4 in the retracted position as the guiding means 9d are provided with a protruding part 30 (see FIGS. 12, 15, 19, 20) on the rearmost half. When the spring unit 13 is biased, this protruding part 30 will be influenced by a downward force created because the carrier body 4 is being pulled forward at a low point.

When the user is going to apply the device the needle unit 2, 4 is brought to a retracted position (see FIG. 10) by pulling the handle 22 either (1) until the projection 23 on the lower side of the handle passes a raised part 24 on the inside of the lower part of the housing 1 or (2) until the protruding part 30 on the guiding means 9d passes the end of or an opening in the L-profiled guiding means 9b of the housing 1. Then the user places the upwardly bend parts 10 against the skin and release the needle unit 2, 4.

When the user wants to release the needle unit 2, 4 from the retracted position the user can push the two pressure points 7 together if the needle unit is locked by (1) or the user can push down at 7a if the needle unit is locked by (2). Preferably there will be indicated pressure points 7a on both upper and lower side of the housing 1 in order for the user to apply oppositely directed finger pressures. When the to points 7 are pushed toward each other the diameter of the housing perpendicular to a line between the pressure points is increased, and as the guiding means 9d on the upper side of the carrier body 4 are caught in the inward L-profiles the projection 23 is lifted free of the raised part 24. This activates the spring unit 13 and causes the needle unit 2, 4 and the attached sensor housing 3 to move forward to an advanced position. When pushing down at 7a the user pushes down the front end of the guiding means 9d and disengage the protruding parts at the rear end of the guiding means 9d from the means 9b of the housing 1, this activates the spring unit 13 and causes the needle unit 2, 4 and the attached sensor housing 3 to move forward to an advanced position.

Figure 11:
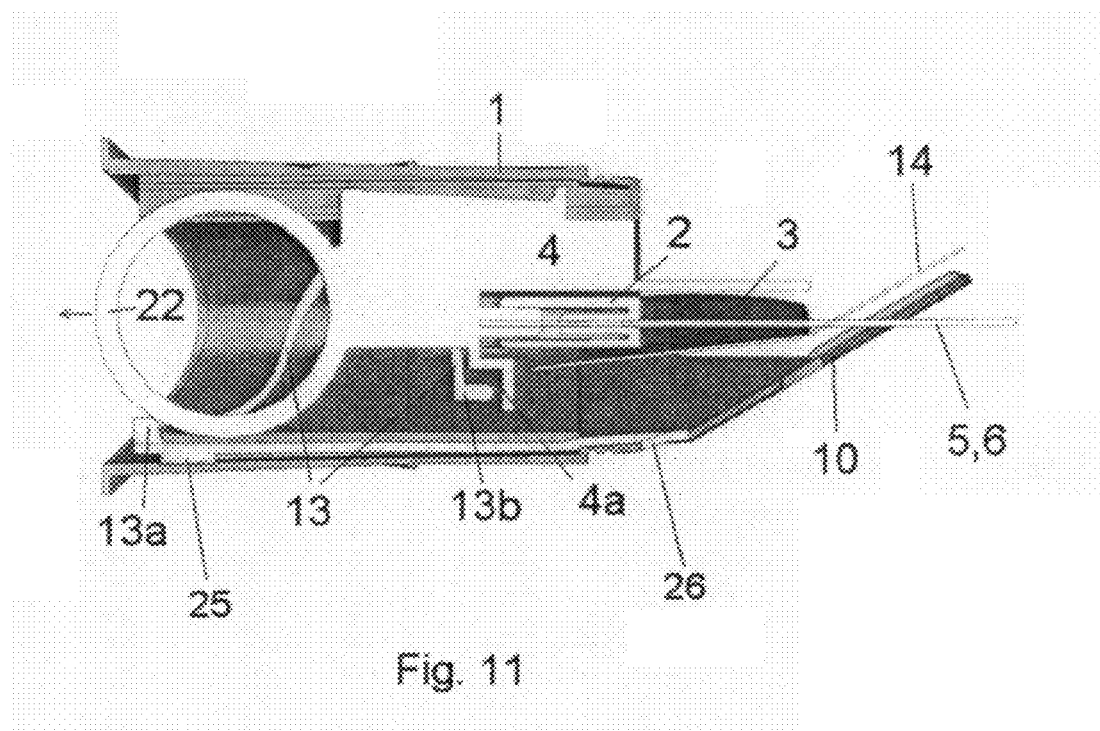
FIG. 11 shows a side view of a fourth embodiment with C-formed spring units.
Figure 12:
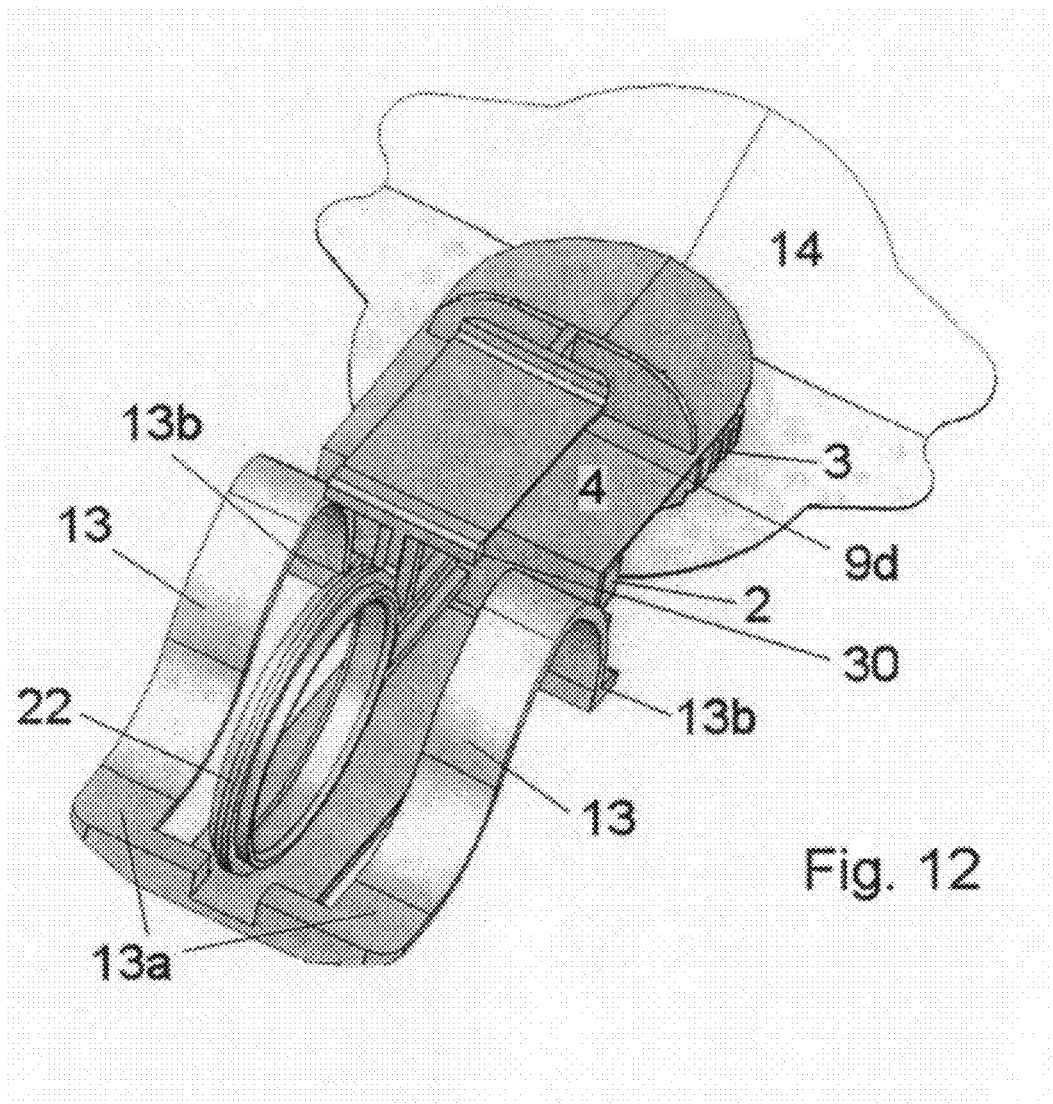
FIG. 12 shows the needle unit combined with the spring unit of the fourth embodiment seen from above/behind.

In FIGS. 11 and 12 is shown a fourth embodiment with a different kind of spring unit 13. The spring unit 13 of this embodiment is made of two flat springs and each of them is formed as a C when the spring unit is unbiased. That the flat springs are formed as a C means that they comprise only one convex curve, how the springs are shaped and fastened at each end, 13a and 13b, of the curve will depend on the material and the form chosen for the springs. The flat springs 13 are fastened to the bottom wall of the housing 1 in such a way that the back end 13a of the C-formed spring units 13 are stationary in relation to the housing 1. The front end 13b of the flat springs rests against a surface 4a of the needle unit 2, 4 or is fastened to the needle unit 2, 4. In this embodiment the C-formed spring units 13 are placed between the back end of the needle unit 2, 4 and the back end of the housing 1 and when the handle 22 is pulled back, the spring units 13 are biased, the two ends of the C-formed spring units, 13a and 13b, are brought closer together. When the release button 17 is activated the spring units 13 will return to the unbiased form and the needle unit 2, 4 will be pushed forward.

In FIG. 12A is shown an embodiment of the flat springs 13 are fastened to the top wall of the housing 1 in such a way that the back end 13a of the slightly C-formed spring units 13 are stationary in relation to the housing 1. The front end 13b of the flat springs rests against a surface of the needle unit 2, 4 or is fastened to the needle unit 2, 4 but the front end 13b is in this embodiment fastened to the front part of the needle unit 2, 4 below the needle level.

How the flat springs are fastened to the housing 1 at 13a will depend on which material they are made of as this influence the form—particularly the thickness—they are made in. If the flat springs are made of a plastic material the material where they are fastened to the housing 1 can take almost any form if they e.g. are produced by molding. If the material is of an adequate thickness a protruding part 25 of the flat spring can be squeezed into an opening in the housing 1. If the flat springs are made of e.g. metal it would be more expensive to form a protruding part 25 on the flat spring, in this case it would in stead be efficient to cut e.g. a three-sided rectangular slit in the flat spring which is to be fastened to the housing 1 and form a cut-out 26. This slit makes it possible to bend the cut-out 26 out of the surface of the flat spring and let it rest against the housing 1. When the flat springs are fastened to the housing 1 either by a protruding part 25 or by a cut-out 26 it will not be necessary to perform further fastening of the springs to the housing e.g. by welding, gluing or the like.

Figure 13:
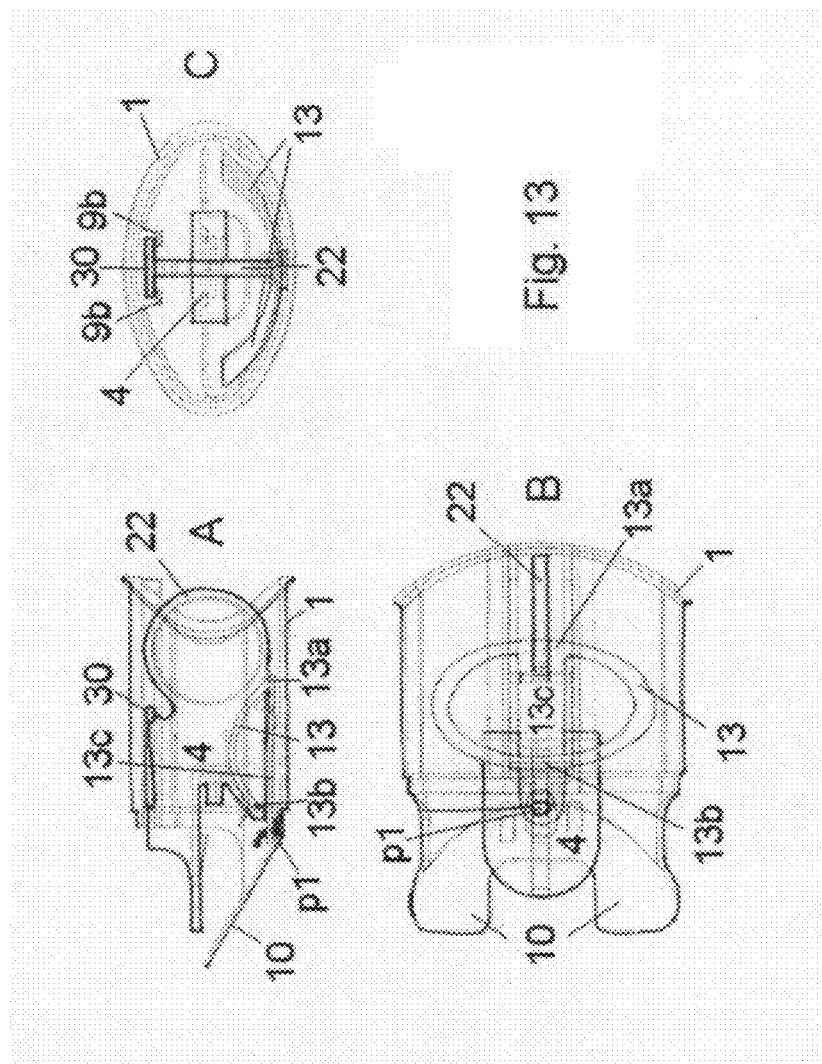
FIG. 13 shows a fifth embodiment with a circular spring seen from the side A, from above B and from behind C.

FIG. 13 shows a fifth embodiment of the inserter where the spring unit 13 is formed of a circular spring. The rearmost part 13a of the circular spring unit 13 is stationary to the housing 1 and the front part 13b of the circular spring 13 is fastened to the needle unit 2, 4 or to the handle 22 or is simply resting against the movable needle unit 2, 4 or handle 22 in a slightly biased state. The spring unit 13 might be formed with a prolonged part 13c lying along the bottom wall of the housing 1. Such a prolonged part 13c could be fastened anyway along its length but preferably at a position p1 close to the front of the housing 1.

FIG. 13A shows an embodiment where the rearmost part 13a of the circular spring unit 13 is resting against the upper part (above needle level) of the housing 1 and the front part 13b of the circular spring 13 is fastened to the handle 22 by simply resting a specially formed part against the handle 22 in a slightly biased state.

Figure 14:
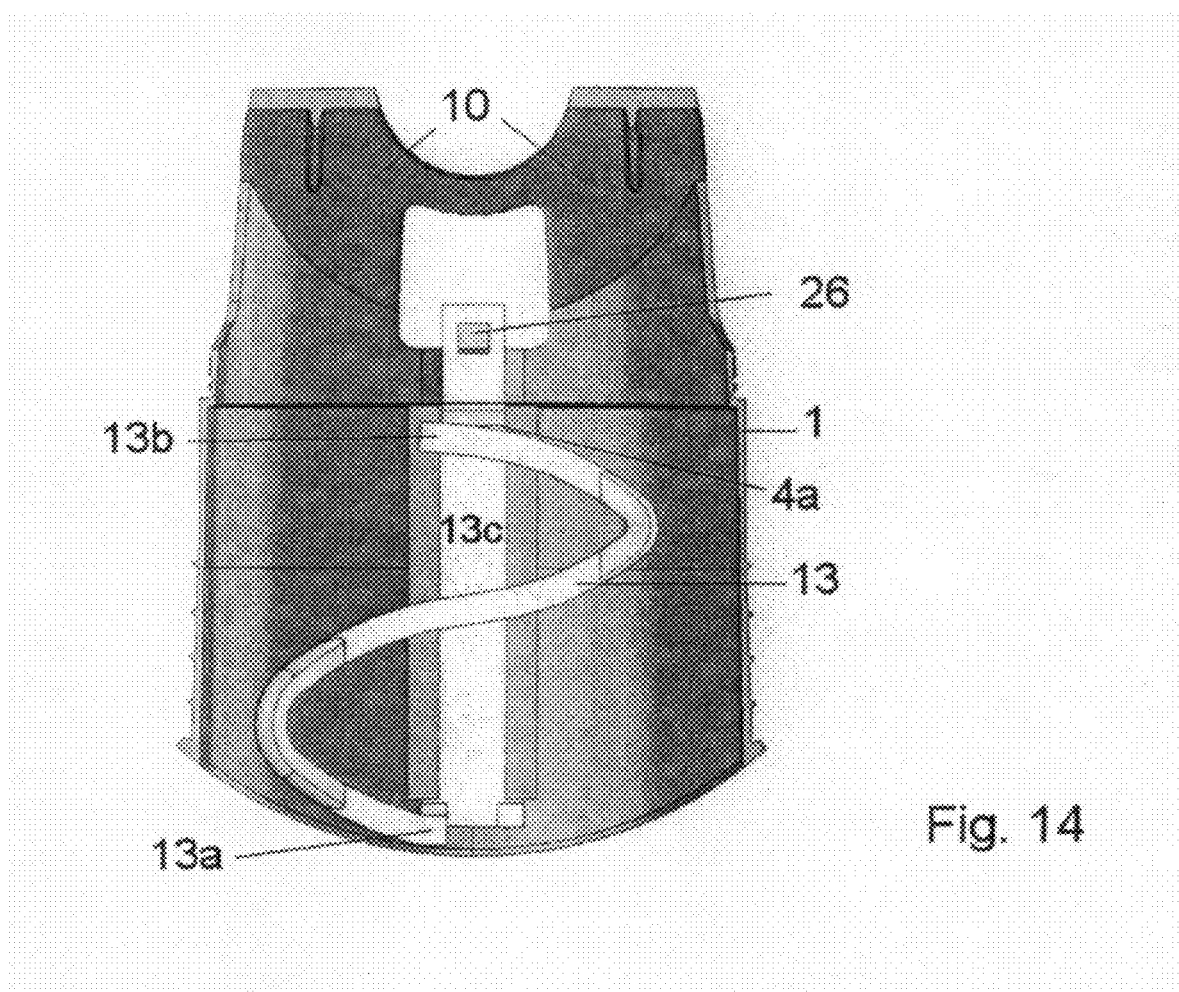
FIG. 14 shows a sixth embodiment with an S-formed spring unit seen from above.

FIG. 14 shows a sixth embodiment with a spring unit 13 formed as an S and constituted of a flat spring made of metal or plastic. The front part 13b of the S-formed spring is fastened to or rests against a surface 4a of the needle unit preferably in a slightly biased state when the needle unit 2, 4 is in its foremost position; the rearmost end of the S-formed spring is fastened to the bottom of the housing 1. Preferably the rearmost end is fastened to the housing by a prolonged part 13c which can be placed in a trail formed by two opposite and inward turned, upright L-profiles, fastened at the rear end e.g. by a protruding part 25 of the spring unit 13 being pressed into an opening in the housing 1, and at the front by a three-sided rectangular slit 26 in the prolonged part forming a cut-out which can catch the front edge of the housing 1. When the handle and the needle unit are pulled back the two ends of the S are pressed together biasing the spring, and when the release button is activated the spring pushes the needle unit 2, 4 forward.

The spring unit 13 according to the sixth embodiment could also be formed as the number 8, have more curves than an ordinary S or more circles than the number 8.

FIG. 15 shows a seventh embodiment of the inserter where the spring unit 13 is formed of a coiled spring. The rearmost part 13a of the coiled spring unit 13 is stationary to the housing 1 and the front part 13b of the coiled spring 13 is fastened to the needle unit 2, 4 or to the handle 22 or is simply resting against a part of the movable needle unit or handle in a slightly biased state. The spring unit 13 might be partly enclosed in a trail lying along the bottom wall of the housing 1. Such a trail would preferably be made of the same material as the housing 1. The trail can consist of to walls rising from the bottom wall of the housing 1, and the walls might be parallel, rounded inwards or inclined toward each other. A part of the needle unit 2, 4 is formed as reaching downwards, and this part reaches down into and slides inside the trail. The front end 13b of the spring unit 13 is fastened to or rest against this part. When the handle 22 is brought to the retracted position, this part will assure that the spring unit 13 inside the trail is biased by pushing the movable end 13b of the spring unit 13 towards the stationary end 13a.

Figure 16:
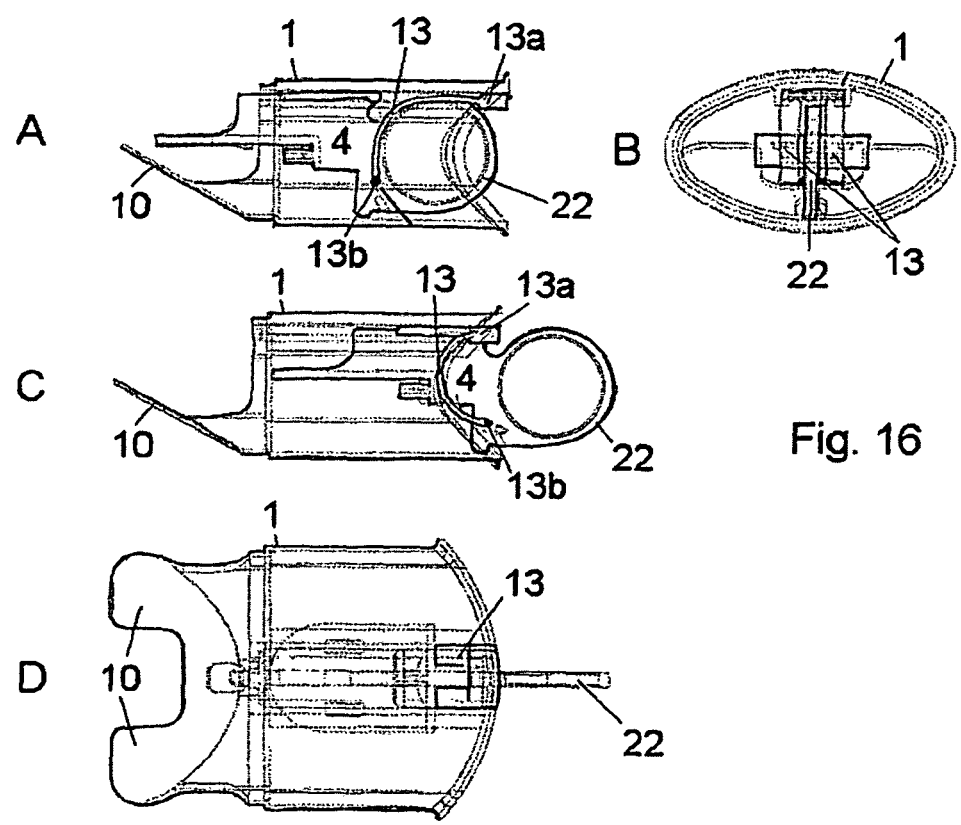
FIG. 16 shows an eighth embodiment with a flat spring in A: a forward position seen from the side, B: a forward position seen from the behind, C: a retracted position seen from the side, D: a retracted position seen from above.

FIG. 16 shows an eighth embodiment of the inserter where the spring unit 13 is a circular or rectangular leaf spring. The back end 13a of this flat spring 13 is stationary to the housing 1, and the back end 13b is fastened or rest against a part of the top wall of the housing 1. The front end 13b is fastened to the lower side of the needle unit 2, 4 e.g. at a position p2 (see FIGS. 9a and 9b).

Figure 17:
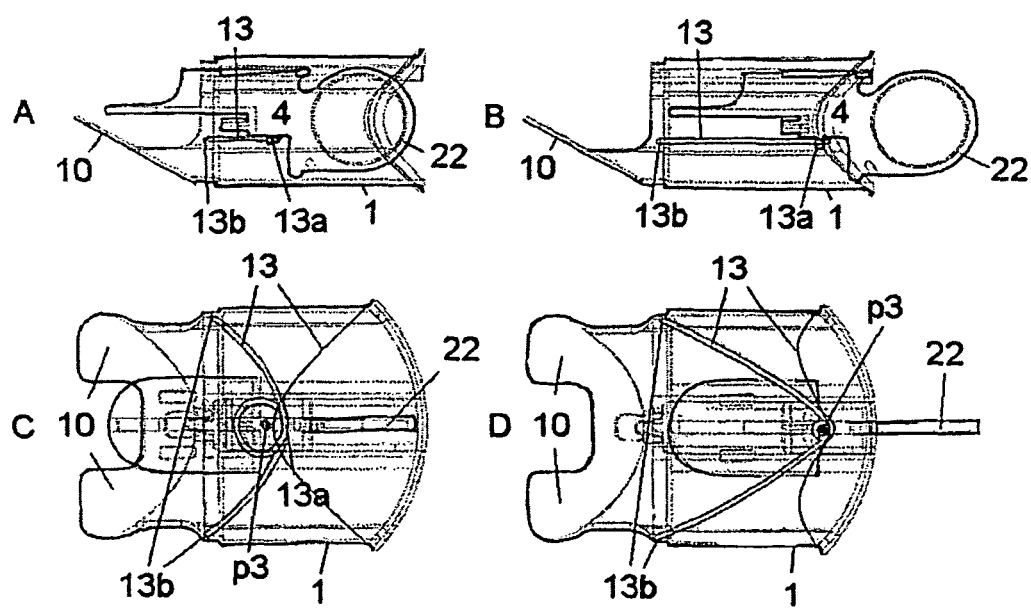
FIG. 17 shows a ninth embodiment with a spring unit fastened to opposite sides of the housing and the embodiment is shown in (A) a forward position seen from the side, (B) a retracted position seen from the side, (C) a forward position seen from above, (D) a retracted position seen from above.

FIG. 17 shows a ninth embodiment of the inserter where the spring unit 13 is fastened to opposite walls of the housing 1. In FIG. 17 the front ends 13b of the spring unit 13 is fastened to the side walls of the housing 1, and the rearmost part 13a of the spring unit 13 is fastened to or rests against the movable needle unit 2, 4 at a position p3. In this embodiment the spring unit 13 forms a loop around a low part of the needle unit 2, 4, and does not actually touch the position p3 when the spring unit is in an unbiased state. When the handle 22 is pulled back biasing the spring unit 13, the loop will be deformed and tightened around the low part of the needle unit 2, 4, and when the release button is activated the needle unit 2, 4 will be pulled forward by the spring unit 13 as the loop will return to its original form. Preferably this embodiment would be made of a metal wire or another material with similar characteristics.

It would also be possible to construct the spring unit 13 of a flat spring where the foremost part is resting against the position p3 and indicated in FIGS. C and D with a thin black line, and the rearmost part is fastened to the side walls of the housing 1 at the rear position of the side walls. In this case the flat spring could be made of metal or plastic.

Figure 18:
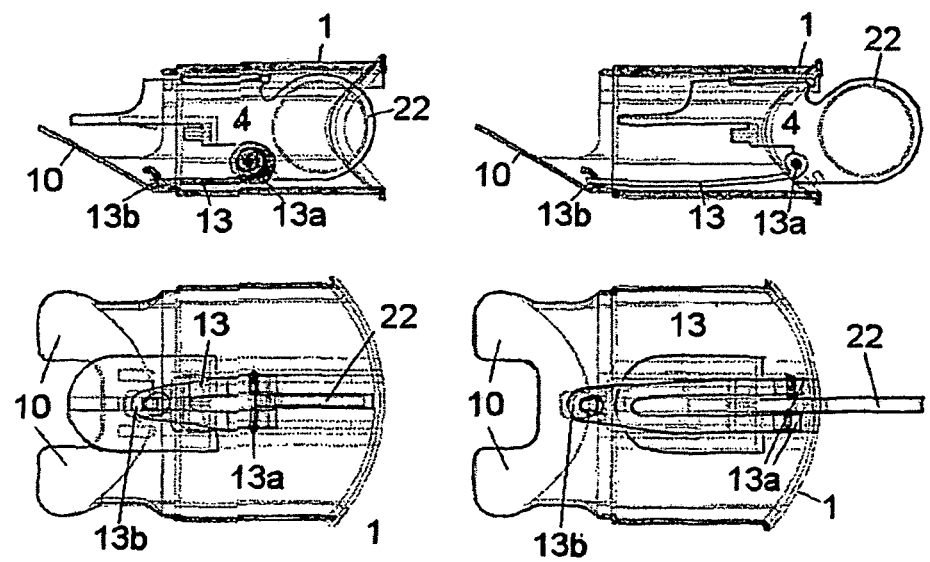
FIG. 18 shows a tenth embodiment of the inserter with a spiral spring unit.

FIG. 18 shows an inserter with a spiral spring 13 where one end 13a of the spring is fixed to a bottom part of the needle unit 2, 4, and the other end 13b is fixed to a hook or similar at the front part of the housing 1. When retracting the needle unit 2, 4 the spiral spring is uncoiled, and when releasing the retainer the spring coils up and moves forward, causing the needle and sensor to pierce the skin at a proper angle and enter into the subcutaneous layer at a proper distance.

A tension spring could be made into a compression spring by passing both spring wire ends through the centre of the coils/turns of the spring to the opposite end of the spring. When pulling the wire ends the spring will compress.

Figure 19:
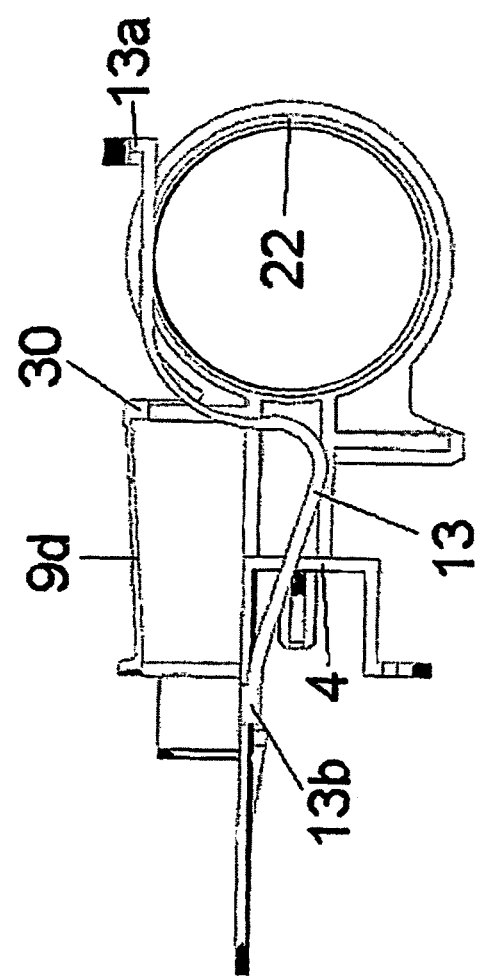
FIG. 19 shows a side view of an eleventh embodiment of an S-formed spring unit.
Figure 20:
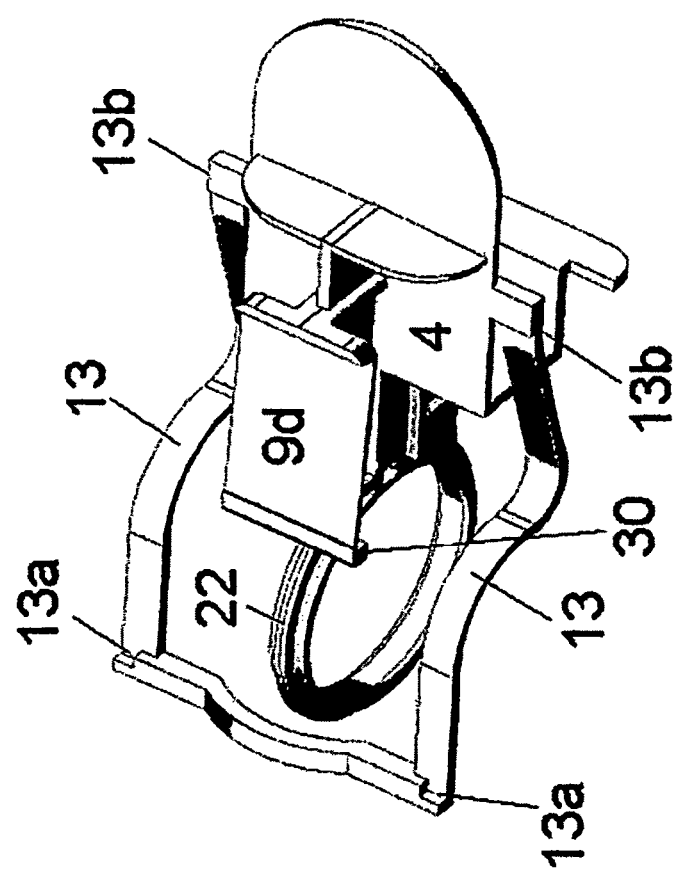
FIG. 20 shows a view from above of the eleventh embodiment of the S-formed spring unit.

In FIGS. 19 and 20 is shown an eleventh embodiment the spring unit 13 is made of two flat springs and each of them is formed as a slightly bend S. That the flat springs are formed as an S means that they comprise two convex curves. The flat springs 13 are fastened to the top wall of the housing 1 in such a way that the back end 13a of the S-formed spring units 13 are stationary in relation to the housing 1. The front ends 13b of the flat springs are fastened to the needle unit 2, 4. In this embodiment the S-formed spring units 13 are placed between the front end of the needle unit 2, 4 and the back end of the housing 1 and when the handle 22 is pulled back, the spring units 13 are biased, the two ends of the S-formed spring units, 13a and 13b, are brought closer together. When the release button 17 is activated the spring units 13 will return to the unbiased form and the needle unit 2, 4 will be pushed forward.

Most of the embodiments of the spring unit shown here are compression springs, except the third embodiment which is provided with a spring unit constituted by an elastic O-ring and the tenth embodiment which is provided with a spring unit constituted by a flat spiral spring; these units are tension springs. The ninth embodiment which is constituted by a round thread works both as a compression and tension spring.

Spring units can e.g. be made of steel and in plastic. Spring units in plastic would preferably be made of POM (Polyoxymethylene), and housing, hard case top and carrier body would preferably be made of PP (Polypropylene). If the spring unit and the carrier body are molded together as one unit the preferred material would be POM.

In this description the expression "flat spring" comprises "leaf spring".

In stead of using a spring unit 13 to bring the needle unit 2, 4 from a retracted to a forward position it would be possible to use magnets. When using magnets repulsive magnets with an adequate repulsive force to move the needle unit 2, 4 from a retracted to a forward position should be chosen. One magnet is placed in the housing 1 and another magnet is placed at the needle unit 2, 4 carrying the infusion device. The repulsion between the magnets will force the needle unit 2, 4 in a forward direction when releasing the needle unit 2, 4 by activating a release button. The magnets can be molded into the housing and into the needle unit respectively in order to protect and hide the magnets. Further the repulsive magnets should be made in different sizes in order to avoid that the magnetic field changes.

FIG. 21a-21c show a transcutaneous sensor known from U.S. Pat. No. 5,954,643, this transcutaneous sensor is prepared for manual insertion. The reference numbers and the names for the different parts used in FIG. 21a-21c and in the corresponding description are identical to the numbers and names originally used in U.S. Pat. No. 5,954,643.

The transcutaneous sensor comprises three separable parts a cable connector 20', a mounting base 30' and a hub 80'. The mounting base 30' is having a generally planar or flat underside surface attached to an adhesive patch 34'. The cable connector 20' defines a socket fitting 92' for mating slide-fit engagement with the rear cable fitting of the mounting base 30'. This socket fitting 92' has a cylindrical entry position 93' which merges with a generally D-shaped or half-circle step portion 94' sized to receive the D-shaped key 50' of the rear cable fitting. The socket fitting 92' includes a plurality of conductive contacts 96' positioned on the step portion 94 for electrically coupled engagement with contact pads on the proximal end segment of a sensor 12', when the mounting base 30' and cable connector 20' are coupled together as viewed in FIG. 21b. When assembled, seal rings 48' provide a sealed connection between the entry portion 93' of the socket fitting 92' and the rear cable fitting of the mounting base 30'. The D-shaped geometry of the interfitting components 50' and 94' insure one-way interconnection for correct conductive coupling of the cable 22' to the sensor 12'. The mounting base 30' and the cable connector 20' are retained in releasably coupled relation by interengaging snap fit latch members. The mounting base 30' includes a pair of rearwardly projecting cantilevered latch arms 97' which terminate at the rearward ends thereof in respective undercut latch tips 98'. The latch arms 97' are sufficiently and naturally resilient for movement relative to the remainder of the mounting base 30', to permit the latch arms 97' to be squeezed inwardly toward each other. The permissible range of motion accommodates snap fit engagement of the latch tips 98' into a corresponding pair of latch recesses 100' formed in the cable connector 20' on opposite sides of the socket fitting 92', wherein the latch recesses 100' are lined with latch keepers 102' for engaging said latch tips 98'. The components can be disengaged for uncoupling when desired by manually squeezing the latch arms 97' inwardly toward each other for release from the latch keepers 102', while axially separating the mounting base 30 from the cable connector 20'.

In this embodiment the sensor 12' is a flexible thin film sensor comprising a relatively thin and elongated element which can be constructed according to so-called thin film mask techniques to include elongated conductive elements. The proximal end segment of the thin film sensor 12' is positioned in a channel in the mounting base 30' the distal end segment of the sensor 12' is positioned along the insertion needle 14'. A cannula 58' is slidably fitted over at least a portion of the proximal end segment of the sensor 12', to extend also over the distal end segment to encase and protect the sensor. In the one embodiment, the cannula is constructed from a lightweight plastic material such as a urethane based plastic and has a double lumen configuration as shown in FIG. 21c. The double lumen cannula 58' is especially suited for slide-fit engagement with and disengagement from the insertion needle 14'.

The hub 80' includes an enlarged tab-like wing 82' adapted for easy grasping and handling between the thumb and index finger. This enlarged wing 82' projects upwardly from a bifurcated nose 84' which is sized and shaped to seat onto the mounting base upper surface 40'.

Signals from the sensor 12' are via the electrical cable 22' coupled to a suitable monitoring or recording device.

FIG. 22-27 shows an inserter according to the present invention adapted to a transcutaneous sensor having a mounting base corresponding to the embodiment described in FIG. 21.

Figure 24:
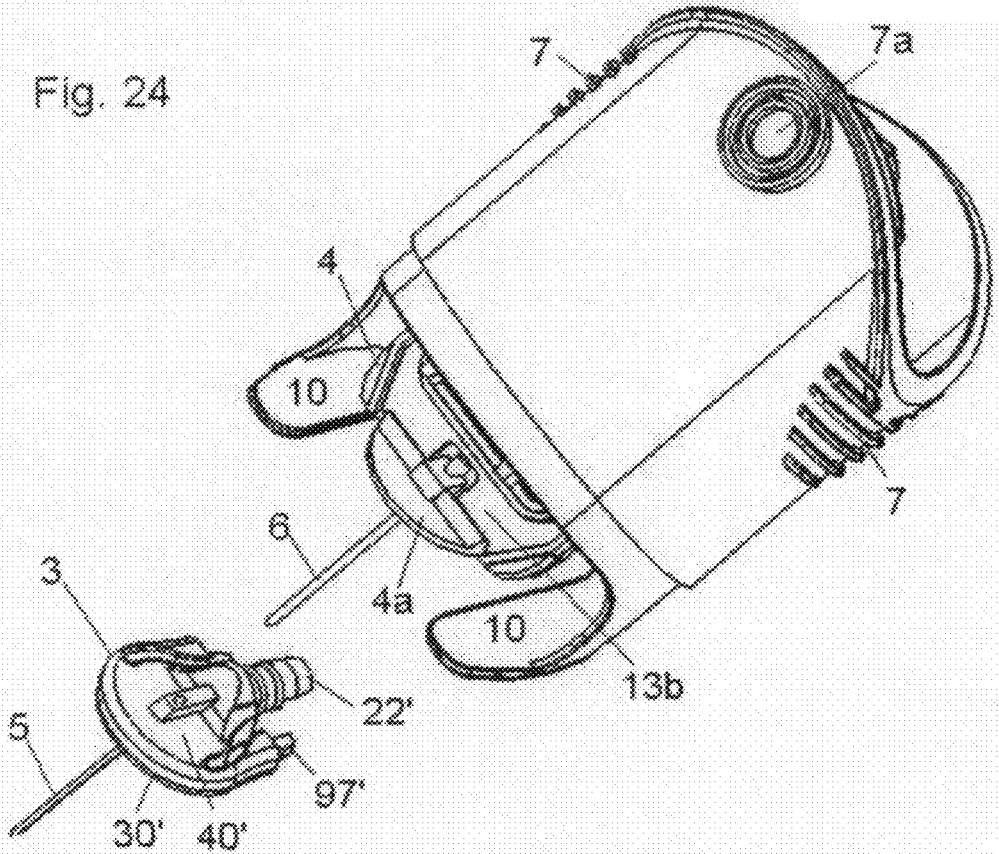
FIG. 24 shows an inserter for a transcutaneous sensor Where the sensor housing has been released from the carrier body of the inserter.

In the embodiment of FIG. 22-24 the carrier body 4 is adapted to carry a sensor housing 3 where the lower surface of the sensor housing 3 i.e. the surface which is closest to the patient during use, is angled relative to the line constituted of the insertion needle 6 and the adjoined sensor part 5. The carrier body 4 has been adapted to carry this embodiment of the sensor housing 3 by forming an angled surface part 4a, this surface part 4a supports the sensor housing 3 during insertion and assures correct positioning of both the laterally projecting insertion needle 6 and the angled lower surface of the sensor housing 3.

Further the embodiments of FIG. 22-24 is adapted to the sensor housing by assuring the distance between the upwardly bend parts 10 is wide enough to let the inclined sensor housing pass through the opening.

Figure 25:
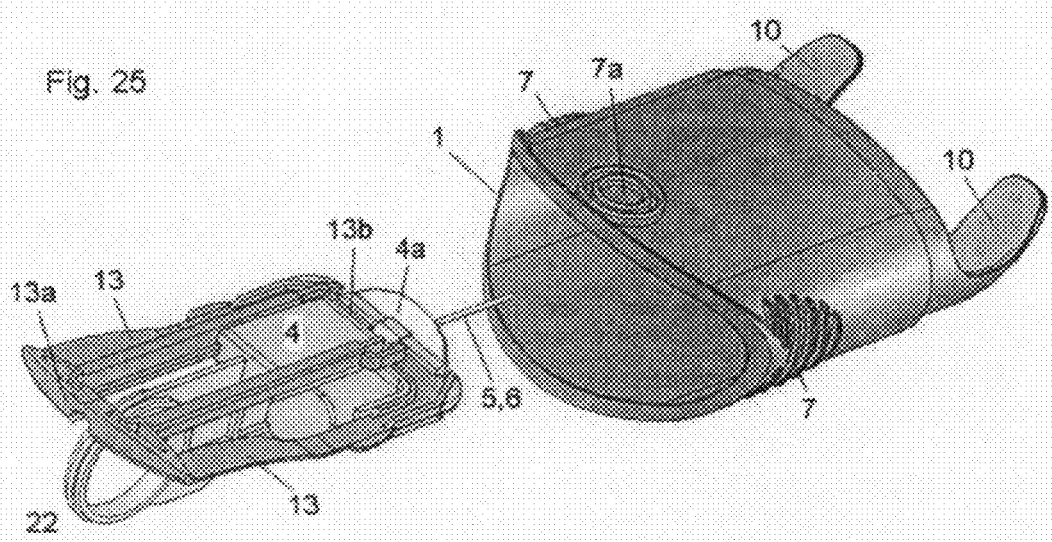
FIG. 25 shows an exploded view of an inserter after release of the sensor housing where the carrier body together with the spring has been removed from the inserter housing.

FIG. 25 shows a carrier body 4 combined with a spring unit. The spring unit according to this embodiment is made of plastic and comprises a spring functioning part 13, secondary fastening means, stop parts for the secondary fastening means and back stop for the secondary fastening means. The spring functioning part 13 comprises two flat springs positioned on opposite sides of the carrier body 4, and the spring functioning parts 13 together with an end piece 13a and a front piece 13b forms a closed ring which makes it strong and easy to handle. When the spring functioning parts 13 are biased and the end piece 13a and the front piece 13b are brought together the spring functioning parts 13, which are here shown in the unbiased form, are bend and form an S- or a C-like curve. In this embodiment the spring unit is fastened to the housing 1 of the inserter by the secondary fastening means which are positioned along the inside top wall of the inserter.

Spring units of the type shown in FIG. 25 can e.g. be made of steel and in plastic. Spring units in plastic could e.g. be made of POM (Polyoxymethylene), and housing 1, hard case top 20 and carrier body 4 could e.g. be made of PP (Polypropylene).

If the spring unit and the carrier body in stead are molded together as one unit a material such as POM could be used.

In stead of using a spring unit to bring the sensor housing 3 from a retracted to a forward position it would be possible to use magnets. When using magnets repulsive magnets with an adequate repulsive force to move the sensor housing 3 from a retracted to a forward position should be chosen. One magnet is placed in the housing 1 and another magnet is placed at the carrier body 4 carrying the sensor housing 3. The repulsion between the magnets will force the sensor housing 3 in a forward direction when releasing the carrier body 4 by activating a release button. The magnets can be molded into the housing 1 and into the carrier body 4 respectively in order to protect and hide the magnets. Further the repulsive magnets should be made in different sizes in order to avoid that the magnetic field changes.

Figures 26, 27:
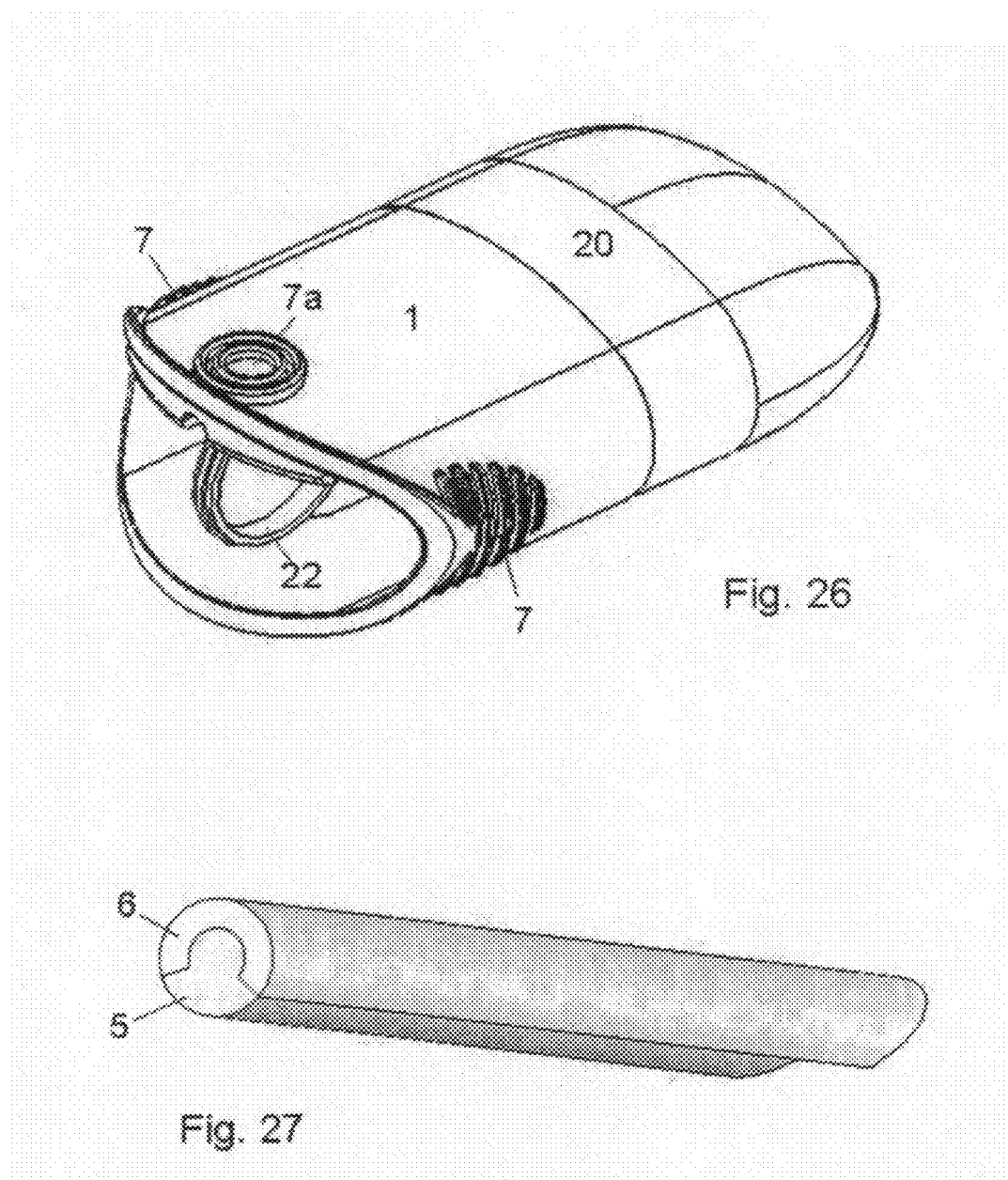
FIG. 26 shows an inserter for a transcutaneous sensor after use with a hard top mounted to protect the surroundings.
FIG. 27 shows an embodiment of an insertion needle combined with a sensor part.

FIG. 26 shows an inserter after use. At this point the user has inserted the sensor housing 3 with the inserter and removed the inserter and thereby the insertion needle 6 from the sensor housing 3. After use the insertion needle 6 is in a forward position and in order to protect the surroundings from the used insertion needle the user has reapplied the hard case top 20.

FIG. 27 shows an embodiment of the insertion needle 6 combined with the sensor part 5.

The invention claimed is:

1. An inserter for a transcutaneous sensor comprising:
    a housing, the housing comprising housing guiding members on an internal surface of the housing;
    a carrier body, the carrier body comprising carrier body guiding members on an external surface of the carrier body, wherein the carrier body guiding members and the housing guiding members guide movement of the carrier body relative to the housing between a retracted and an advanced position;
    a needle hub comprising an insertion needle for piercing of the skin and an unreleasable locking member for interacting with a corresponding locking member on the carrier body;
    a sensor housing comprising a sensor part configured for subcutaneous placement, the sensor housing and the needle hub being releasably connected to each other, wherein the insertion needle is adjoined to the sensor part when the sensor housing and the needle hub are connected, wherein the insertion needle has a proximal and distal end along a longitudinal axis, wherein the sensor part has a proximal and distal end along the longitudinal axis therebetween, and wherein the needle at least partly surrounds the sensor part along the longitudinal axis; and
    a spring unit connected to a release member, the release member being activatable so that the spring unit moves the sensor housing, the needle hub and the carrier body to an advanced position for subcutaneous placement of the needle and sensor part.

2. The inserter according to claim 1, wherein the needle hub and the carrier body are created as a single unit.

3. The inserter according to claim 1, wherein the needle hub comprises openings and the carrier body is provided with projections corresponding to the openings in the needle hub.

4. The inserter according to claim 1, wherein a needle unit comprising the needle hub and the carrier body after insertion can be placed in a retracted position.

5. The inserter according to claim 1, wherein a lower base of the housing is formed with a projecting part.

6. The inserter according to claim 5, wherein the projecting part forms an angle with the longitudinal direction of the insertion needle.

7. The inserter according to claim 1, wherein the inserter further comprises a stopper.

8. The inserter according to claim 7, wherein the stopper comprises at least one end of a track for a flange.

9. The inserter as claimed in claim 1, wherein the housing forms at least a part of the delivery packing for the inserter.

10. The inserter as claimed in claim 1, wherein the housing is provided with a substantially rigid cover.

11. The inserter as claimed in claim 1, wherein the spring unit is fastened to the housing in a first position and to the carrier body or the needle hub in a second position, and the first position is situated closer to a front end of the housing than the second position when the spring unit is unbiased.

12. The inserter as claimed in claim 1, wherein the spring unit is an elastic O-ring.

13. The inserter as claimed in claim 1, wherein the spring unit is fastened to the housing in a first position and fixed to the carrier body or the needle hub in a second position, and the first position is situated closer to a back end of the housing than the second position when the spring unit is unbiased.

14. The inserter as claimed in claim 1, wherein the spring unit is a flat spring placed between a back end of the housing and a needle unit.

15. The inserter as claimed in claim 14, wherein the spring unit comprises two convex curves placed on each side of the needle unit, and that each curve is fixed to the needle unit at one end and to the housing behind the fixation to the needle unit at another end in the unbiased state.

16. An inserter for a transcutaneous sensor comprising:
a set housing, the housing comprising housing guiding members on an internal surface of the housing;
a carrier body, the carrier body comprising carrier body guiding members on an external surface of the carrier body, wherein the carrier body guiding members and the housing guiding members guide movement of the carrier body relative to the housing between a retracted and an advanced position;
a needle hub comprising an insertion needle for piercing of the skin and an unreleasable locking member for interacting with a corresponding locking member on the carrier body;
a sensor housing comprising a sensor part configured for subcutaneous placement, the sensor housing and the needle hub being releasably connected to each other, wherein the insertion needle is adjoined to the sensor part when the sensor housing and the needle hub are connected, wherein the insertion needle has a proximal and distal end along a longitudinal axis, wherein the sensor part has a proximal and distal end along the longitudinal axis therebetween, and wherein the needle at least partly surrounds the sensor part along the longitudinal axis; and
a spring unit connected to a release member, the release member being activatable so that the spring unit moves the sensor housing, the needle hub and the carrier body to an advanced position for subcutaneous placement of the needle and sensor part;
and a lower base of the housing comprising a projecting part, the projecting part forming an angle with a longitudinal direction of the insertion needle indicating a correct insertion angle for the user during insertion.

17. The inserter as claimed in claim 16 wherein a part of the projecting part is positioned above the line along which the insertion needle can move and a part of the projecting part is positioned beyond said line.

18. A method of inserting a sensor for detecting glucose in the blood of a patient, the method comprising:
providing an inserter of claim 1;
releasing the release member to activate the spring unit;
inserting the sensor part into the skin of the patient; and
removing the inserter from the sensor part while maintaining subcutaneous placement of the sensor part.

* * * * *